(12) United States Patent
Dai et al.

(10) Patent No.: US 7,812,166 B2
(45) Date of Patent: Oct. 12, 2010

(54) KINASE INHIBITORS

(75) Inventors: Yujia Dai, Gurnee, IL (US); Kresna Hartandi, Los Angeles, CA (US); Michael R. Michaelides, Libertyville, IL (US)

(73) Assignee: Abbott Laboratories, Abbott Park, IL (US)

( * ) Notice: Subject to any disclaimer, the term of this patent is extended or adjusted under 35 U.S.C. 154(b) by 453 days.

(21) Appl. No.: 11/261,814

(22) Filed: Oct. 28, 2005

(65) Prior Publication Data
US 2006/0178378 A1     Aug. 10, 2006

Related U.S. Application Data

(60) Provisional application No. 60/623,175, filed on Oct. 29, 2004.

(51) Int. Cl.
C07D 471/02     (2006.01)

(52) U.S. Cl. .................................................. 546/113

(58) Field of Classification Search ............... 544/238, 544/241, 242, 336; 546/117, 119, 113
See application file for complete search history.

(56) References Cited

U.S. PATENT DOCUMENTS 4,260,621 A * 4/1981 Roch et al. ................. 514/303

FOREIGN PATENT DOCUMENTS

| DE | 22 38 400 | 2/1974 |
|---|---|---|
| DE | 26 43 753 | 4/1978 |
| WO | 97/42187 | 11/1997 |
| WO | 01/19828 | 3/2001 |
| WO | 02/088078 | 11/2002 |
| WO | 03/080064 | 10/2003 |
| WO | 2004/113304 | 12/2004 |
| WO | 2006050109 | 5/2006 |

OTHER PUBLICATIONS

Witherington et al., Bioorganic & Medicinal Chemistry Letters, (2003), 13(9), 1577-1580.*
Attaby et al., Phosphorus, Sulfur and Silicon and the Related Elements, (1999), 149, 49-64.*
Attaby et al., Archives of Pharmacal Research (1999), 22(2), 194-201.*
Al-Omran et al., Heteroatom Chemistry (1995), 6(6), 545-52.*
Bomika et al., Khimiya Geterotsiklicheskikh Soedinenii, (1976), (8), 1085-8.*
Attaby et al., "Synthesis and antimicorbial evaluation of several new pyridine, thienopyridine and pyridothienopyrazole derivatives," Phosphorus, Sulfur and silicon and the Related Elements, Gordon and Breach Science Publishers, Amsterdam, 1999.
Brana Miguel et al. "Pyrazolo[3,4-c]pyridazines as novel and selective inhibitors of cyclin-dependent kinases," Journal of Medicinal Chemistry 48(22):6843-6854 (2005).
Cullinan-Bove et al., "Vascular endothelial growth factor/vascular permeability factor expression in the rat uterus: rapid stimulation by estrogen correlates with estrogen-inuced increases in uterine capillary permeability and growth," Endocrinology 133(2):829-837 (1993).
Eldin et al., "Cyanothioacetamide and its derivatives inj heterocyclic synthesis: synthesis and biological evaluation of some new pyridine and annelated pyridine deritives," Egypt. J. Pharm. Sci. 39(1-3):197-209 (1998).
Elnagdi et al., "Pyrimidine Derivates and Related Compounds a novel synthesis of pyrimidines pyrazolo-4-3-d-pyrimidines and isoxazolo-4-3-d-pyrimidine," Journal of Heterocyclic Chemistry 16(6):1109-1112 (1979).
Elneairy et al., "Synthesis of thiazole, triazole, pyrazolo[3,4-13]-pyridinyl-3-phenylthiourea, aminopyrazolo[3,4-b]pyridine derivatives and their biological evaluation," Phosphorus, Sulfur and Silicon and the Related Elements 167:161-179 (2000).
Kolb et al., "Tyrosine kinase assays adapted to homogeneous time-resolved fluorescence," Drug Discovery Today 3(7):333-342 (1998).
Mathis, "HTRF® Technology," Journal of Biomolecular Screening 4(6):309-314 (1999).
Songyang et al., "Catalytic specificity of protein-tyrosine kinases is critical for slective signaling," Nature 373:536-539 (1995).
Thistlethwaite et al., "Human angiopoietin gene expression is a marker for severity of pulmonary hypertension in patients undergoing pulmonary thromboendarterectomy," Journal of Thoracic and Cardiovascular Surgery 122(1):65-73 (2001).
Tyle, "Iontophoretic devices for drug delivery," Pharmaceutical Research 3(6): 318-326 (1986).
Witherington, et al., "5-aryl-pyrazolo[3,4-b]pyridines: potent inhibitors of glycogen synthase kinase-3 (GSK-3)," Bioorganic & Medicinal Chemistry Letters 13:1577-1580 (2003).
International Search Report for PCT/US2005/038958 dated Jun. 1, 2006.
International Preliminary Report on Patentability with Written Opinion for PCT/US2005/038958 dated May 1, 2007.

* cited by examiner

*Primary Examiner* — D. Margaret Seaman
*Assistant Examiner* — Niloofar Rahmani
(74) *Attorney, Agent, or Firm* — Glen J. Gesicki

(57) ABSTRACT

Compounds having the formula

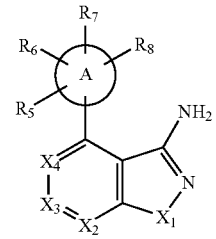

are useful for inhibiting protein tyrosine kinases. The present invention also discloses methods of making the compounds, compositions containing the compounds, and methods of treatment using the compounds.

4 Claims, No Drawings

KINASE INHIBITORS

This application claims priority from U.S. Provisional Patent Application No. 60/623,175, filed on Oct. 29, 2004.

TECHNICAL FIELD

The present invention relates to compounds which are useful for inhibiting protein tyrosine kinases, methods of making the compounds, compositions containing the compounds, and methods of treatment using the compounds.

BACKGROUND OF THE INVENTION

Protein tyrosine kinases (PTKs) are enzymes which catalyse the phosphorylation of specific tyrosine residues in cellular proteins. This post-translational modification of these substrate proteins, often enzymes themselves, acts as a molecular switch regulating cell proliferation, activation, or differentiation. Aberrant or excessive PTK activity has been observed in many disease states including benign and malignant proliferative disorders as well as diseases resulting from inappropriate activation of the immune system (e.g., autoimmune disorders), allograft rejection, and graft vs. host disease. In addition, endothelial-cell specific receptor PTKs such as KDR and Tie-2 mediate the angiogenic process, and are thus involved in supporting the progression of cancers and other diseases involving inappropriate vascularization (e.g., diabetic retinopathy, choroidal neovascularization due to age-related macular degeneration, psoriasis, arthritis, retinopathy of prematurity, and infantile hemangiomas).

The identification of effective small compounds which specifically inhibit signal transduction and cellular proliferation by modulating the activity of tyrosine kinases to regulate and modulate abnormal or inappropriate cell proliferation, differentiation, or metabolism is therefore desirable. In particular, the identification of methods and compounds that specifically inhibit the function of a tyrosine kinase which is essential for antiogenic processes or the formation of vascular hyperpermeability leading to edema, ascites, effusions, exudates, and macromolecular extravasation and matrix deposition as well as associated disorders would be beneficial.

SUMMARY OF THE INVENTION

In its principle embodiment the present invention provides a compound of formula (I)

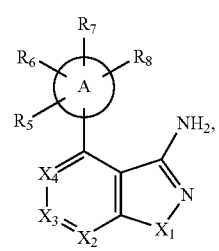

(I)

or a therapeutically acceptable salt thereof, wherein

A is selected from the group consisting of furyl, indazolyl, indolyl, phenyl, pyrazinyl, pyridazinyl, pyridinyl, pyrimidinyl, and thienyl;

$X_1$ is selected from the group consisting of O, S, and $NR_1$;

$X_2$ is selected from the group consisting of N and $CR_2$;

$X_3$ is selected from the group consisting of N and $CR_3$;

$X_4$ is selected from the group consisting of N and $CR_4$;

provided that at least one of $X_2$, $X_3$, and $X_4$ is N;

$R_1$ is selected from the group consisting of hydrogen, alkoxyalkyl, alkoxycarbonyl, alkenyl, alkyl, alkylcarbonyl, aryl, arylalkyl, heteroaryl, heteroarylalkyl, heterocyclealkyl, hydroxyalkyl, $(NR_AR_B)$carbonyl, $(NR_AR_B)$sulfonyl, and $(NR_AR_B)$sulfonylalkyl;

$R_2$ is selected from the group consisting of hydrogen, alkoxy, alkoxyalkoxy, alkoxyalkyl, alkyl, aryl, arylalkyl, aryloxy, aryloxyalkyl, halo, haloalkoxy, haloalkyl, heteroaryl, heteroarylalkenyl, heteroarylalkoxy, heteroarylealkyl, heteroaryloxyalkyl, heterocycle, heterocyclealkenyl, heterocyclealkoxy, heterocyclealkyl, heterocycleoxyalkyl, hydroxy, hydroxyalkoxy, hydroxyalkyl, $(NR_CR_D)$alkenyl, $(NR_CR_D)$alkoxy, $(NR_CR_D)$alkyl, $(NR_CR_D)$alkynyl, $(NR_CR_D)$carbonylalkenyl, and $(NR_CR_D)$carbonylalkyl;

$R_3$ and $R_4$ are independently selected from the group consisting of hydrogen, alkoxy, alkoxyalkoxy, alkoxyalkyl, alkyl, arylalkyl, aryloxy, aryloxyalkyl, halo, haloalkoxy, haloalkyl, heteroarylalkenyl, heteroarylalkoxy, heteroarylealkyl, heteroaryloxyalkyl, heterocycle, heterocyclealkenyl, heterocyclealkoxy, heterocyclealkyl, heterocycleoxyalkyl, hydroxy, hydroxyalkoxy, hydroxyalkyl, $(NR_CR_D)$alkenyl, $(NR_CR_D)$alkoxy, $(NR_CR_D)$alkyl, $(NR_CR_D)$alkynyl, $(NR_CR_D)$carbonylalkenyl, and $(NR_CR_D)$carbonylalkyl;

$R_5$, $R_6$, and $R_7$ are independently selected from the group consisting of hydrogen, alkoxy, alkoxyalkoxy, alkyl, halo, haloalkoxy, haloalkyl, hydroxy, and —$NR_ER_F$;

$R_8$ is selected from the group consisting hydrogen, alkoxy, alkoxyalkoxy, alkyl, halo, haloalkoxy, haloalkyl, hydroxy, and $LR_9$;

$R_9$ is selected from the group consisting of hydrogen, alkyl, aryl, cycloalkyl, heteroaryl, and heterocycle;

L is selected from the group consisting of $(CH_2)_mN(R_{10})C(O)N(R_{11})(CH_2)_n$ and $CH_2C(O)NR_{10}$, wherein each group is drawn with its left end attached to A;

m and n are independently 0 or 1;

$R_{10}$ and $R_{11}$ are independently selected from the group consising of hydrogen and alkyl;

$R_A$ and $R_B$ are independently selected from the group consisting of hydrogen and alkyl;

$R_C$ and $R_D$ are independently selected from the group consisting of hydrogen, alkenyl, alkyl, alkylcarbonyl, alkylsulfonyl, aryl, arylalkyl, arylcarbonyl, arylsulfonyl, haloalkylsulfonyl, cycloalkyl, cycloalkylalkyl, heteroaryl, heteroarylalkyl, heteroarylsulfonyl, heterocycle, heterocyclealkyl, and heterocyclesulfonyl;

$R_E$ and $R_F$ are independently selected from the group consisting of hydrogen, alkyl, and alkylcarbonyl.

In another embodiment, the present invention provides a pharmaceutical composition comprising a compound of formula (I), or a therapeutically acceptable salt thereof, in combination with a therapeutically acceptable carrier.

In another embodiment, the present invention provides a method for inhibiting protein kinase in a patient in recognized need of such treatment comprising administering to the patient a therapeutically acceptable amount of a compound of formula (I), or a therapeutically acceptable salt thereof.

In another embodiment, the present invention provides a method for treating cancer in a patient in recognized need of such treatment comprising administering to the patient a therapeutically acceptable amount of a compound of formula (I), or a therapeutically acceptable salt thereof.

DETAILED DESCRIPTION OF THE INVENTION

In another embodiment, the present invention provides a compound of formula (I) wherein A is furyl; and $X_1$, $X_2$, $X_3$, $X_4$, $R_5$, $R_6$, $R_7$, and $R_8$ are as defined in formula (I).

In another embodiment, the present invention provides a compound of formula (I) wherein A is furyl; $R_8$ is $LR_9$; L is $(CH_2)_mN(R_{10})C(O)N(R_{11})(CH_2)_n$; m is 0; n is 0; $R_9$ is aryl wherein the aryl is phenyl substituted with 0,1, or 2 substituents selected from the group consisting of hydrogen, alkoxy, alkoxycarbonyl, alkyl, carboxy, cyano, halo, haloalkoxy, haloalkyl, hydroxy, hydroxyalkyl, nitro, and —$NR_GR_H$; $X_1$ is $NR_1$; $R_1$ is selected from the group consisting of hydrogen and alkyl; and $R_G, R_H, X_2, X_3, X_4, R_5, R_6, R_7, R_{10}$, and $R_{11}$ are as defined in formula (I).

In another embodiment, the present invention provides a compound of formula (I) wherein A is indazolyl; and $X_1, X_2, X_3, X_4, R_5, R_6, R_7$, and $R_8$ are as defined in formula (I).

In another embodiment, the present invention provides a compound of formula (I) wherein A is indazolyl; $R_8$ is $LR_9$; L is $(CH_2)_mN(R_{10})C(O)N(R_{11})(CH_2)_n$; m is 0; n is 0; $R_9$ is aryl wherein the aryl is phenyl substituted with 0,1, or 2 substituents selected from the group consisting of hydrogen, alkoxy, alkoxycarbonyl, alkyl, carboxy, cyano, halo, haloalkoxy, haloalkyl, hydroxy, hydroxyalkyl, nitro, and —$NR_GR_H$; $X_1$ is $NR_1$; $R_1$ is selected from the group consisting of hydrogen and alkyl; and $R_G, R_H, X_2, X_3, X_4, R_5, R_6, R_7, R_{10}$, and $R_{11}$ are as defined in formula (I).

In another embodiment, the present invention provides a compound of formula (I) wherein A is indolyl; and $X_1, X_2, X_3, X_4, R_5, R_6, R_7$, and $R_8$ are as defined in formula (I).

In another embodiment, the present invention provides a compound of formula (I) wherein A is indolyl; $R_8$ is $LR_9$; L is $(CH_2)_mN(R_{10})C(O)N(R_{11})(CH_2)_n$; m is 0; n is 0; $R_9$ is aryl wherein the aryl is phenyl substituted with 0,1, or 2 substituents selected from the group consisting of hydrogen, alkoxy, alkoxycarbonyl, alkyl, carboxy, cyano, halo, haloalkoxy, haloalkyl, hydroxy, hydroxyalkyl, nitro, and —$NR_GR_H$; $X_1$ is $NR_1$; $R_1$ is selected from the group consisting of hydrogen and alkyl; and $R_G, R_H, X_2, X_3, X_4, R_5, R_6, R_7, R_{10}$, and $R_{11}$ are as defined in formula (I).

In another embodiment, the present invention provides a compound of formula (I) wherein A is pyrazinyl; and $X_1, X_2, X_3, X_4, R_5, R_6, R_7$, and $R_8$ are as defined in formula (I).

In another embodiment, the present invention provides a compound of formula (I) wherein A is pyrazinyl; $R_8$ is $LR_9$; L is $(CH_2)_mN(R_{10})C(O)N(R_{11})(CH_2)_n$; m is 0; n is 0; $R_9$ is aryl wherein the aryl is phenyl substituted with 0, 1, or 2 substituents selected from the group consisting of hydrogen, alkoxy, alkoxycarbonyl, alkyl, carboxy, cyano, halo, haloalkoxy, haloalkyl, hydroxy, hydroxyalkyl, nitro, and —$NR_GR_H$; $X_1$ is $NR_1$; $R_1$ is selected from the group consisting of hydrogen and allyl; and $R_G, R_H, X_2, X_3, X_4, R_5, R_6, R_7, R_{10}$, and $R_{11}$ are as defined in formula (I).

In another embodiment, the present invention provides a compound of formula (I) wherein A is pyridazinyl; and $X_1, X_2, X_3, X_4, R_5, R_6, R_7$, and $R_8$ are as defined in formula (I).

In another embodiment, the present invention provides a compound of formula (I) wherein A is pyridazinyl; $R_8$ is $LR_9$; L is $(CH_2)_mN(R_{10})C(O)N(R_{11})(CH_2)_n$; m is 0; n is 0; $R_9$ is aryl wherein the aryl is phenyl substituted with 0, 1, or 2 substituents selected from the group consisting of hydrogen, alkoxy, alkoxycarbonyl, alkyl, carboxy, cyano, halo, haloalkoxy, haloalkyl, hydroxy, hydroxyalkyl, nitro, and —$NR_GR_H$; $X_1$ is $NR_1$; $R_1$ is selected from the group consisting of hydrogen and alkyl; and $R_G, R_H, X_2, X_3, X_4, R_5, R_6, R_7, R_{10}$, and $R_{11}$ are as defined in formula (I).

In another embodiment, the present invention provides a compound of formula (I) wherein A is pyridinyl; and $X_1, X_2, X_3, X_4, R_5, R_6, R_7$, and $R_8$ are as defined in formula (I).

In another embodiment, the present invention provides a compound of formula (I) wherein A is pyridinyl; $R_8$ is $LR_9$; L is $(CH_2)_mN(R_{10})C(O)N(R_{11})(CH_2)_n$; m is 0; n is 0; $R_9$ is aryl wherein the aryl is phenyl substituted with 0, 1, or 2 substituents selected from the group consisting of hydrogen, alkoxy, alkoxycarbonyl, alkyl, carboxy, cyano, halo, haloalkoxy, haloalkyl, hydroxy, hydroxyalkyl, nitro, and —$NR_GR_H$; $X_1$ is $NR_1$; $R_1$ is selected from the group consisting of hydrogen and alkyl; and $R_G, R_H, X_2, X_3, X_4, R_5, R_6, R_7, R_{10}$, and $R_{11}$, are as defined in formula (I).

In another embodiment, the present invention provides a compound of formula (I) wherein A is pyrimidinyl; and $X_1, X_2, X_3, X_4, R_5, R_6, R_7$, and $R_8$ are as defined in formula (I).

In another embodiment, the present invention provides a compound of formula (I) wherein A is pyrimidinyl; $R_8$ is $LR_9$; L is $(CH_2)_mN(R_{10})C(O)N(R_{11})(CH_2)_n$; m is 0; n is 0; $R_9$ is aryl wherein the aryl is phenyl substituted with 0, 1, or 2 substituents selected from the group consisting of hydrogen, alkoxy, alkoxycarbonyl, alkyl, carboxy, cyano, halo, haloalkoxy, haloalkyl, hydroxy, hydroxyalkyl, nitro, and —$NR_GR_H$; $X_1$ is $NR_1$; $R_1$ is selected from the group consisting of hydrogen and alkyl; and $R_G, R_H, X_2, X_3, X_4, R_5, R_6, R_7, R_{10}$, and $R_{11}$, are as defined in formula (I).

In another embodiment, the present invention provides a compound of formula (I) wherein A is thienyl; and $X_1, X_2, X_3, X_4, R_5, R_6, R_7$, and $R_8$ are as defined in formula (I).

In another embodiment, the present invention provides a compound of formula (I) wherein A is thienyl; $R_8$ is $LR_9$; L is $(CH_2)_mN(R_{10})C(O)N(R_{11})(CH_2)_n$; m is 0; n is 0; $R_9$ is aryl wherein the aryl is phenyl substituted with 0, 1, or 2 substituents selected from the group consisting of hydrogen, alkoxy, alkoxycarbonyl, alkyl, carboxy, cyano, halo, haloalkoxy, haloalkyl, hydroxy, hydroxyalkyl, nitro, and —$NR_GR_H$; $X_1$ is $NR_1$; $R_1$ is selected from the group consisting of hydrogen and alkyl; and $R_G, R_H, X_2, X_3, X_4, R_5, R_6, R_7, R_{10}$, and $R_{11}$ are as defined in formula (I).

In another embodiment, the present invention provides a compound of formula (I) wherein A is phenyl; and $X_1, X_2, X_3, X_4, R_5, R_6, R_7$, and $R_8$ are as defined in formula (I).

In another embodiment, the present invention provides a compound of formula (I) wherein A is phenyl; $R_8$ is hydrogen; and $X_1, X_2, X_3, X_4, R_5, R_6$, and $R_7$ are as defined in formula (I).

In another embodiment, the present invention provides a compound of formula (I) wherein A is phenyl; $R_8$ is $LR_9$; L is $(CH_2)_mN(R_{10})C(O)N(R_{11})(CH_2)_n$; m is 0; n is 0; $R_9$ is heteroaryl; $R_1$ is selected from the group consisting of hydrogen and alkyl; and $X_2, X_3, X_4, R_5, R_6, R_7, R_{10}$, and $R_{11}$ are as defined in formula (I).

In another embodiment, the present invention provides a compound of formula (II)

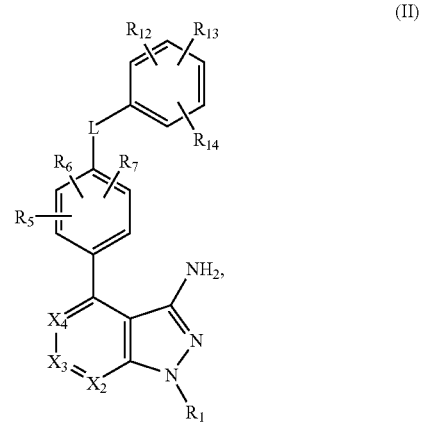

(II)

or a therapeutically acceptable salt thereof, wherein $X_2$ is selected from the group consisting of N and $CR_2$;
$X_3$ is selected from the group consisting of N and $CR_3$;
$X_4$ is selected from the group consisting of N and $CR_4$;
provided that at least one of $X_2, X_3$, and $X_4$ is N;
$R_1$ is selected from the group consisting of hydrogen, alkoxyalkyl, alkoxycarbonyl, alkenyl, alkyl, alkylcarbonyl, aryl, arylalkyl, heteroaryl, heteroarylalkyl, heterocyclealkyl, hydroxyalkyl, $(NR_AR_B)$carbonyl, $(NR_AR_B)$sulfonyl, and $(NR_AR_B)$sulfonylalkyl;

$R_2$ is selected from the group consisting of hydrogen, alkoxy, alkoxyalkoxy, alkoxyalkyl, alkyl, aryl, arylalkyl, aryloxy, aryloxyalkyl, halo, haloalkoxy, haloalkyl, heteroaryl, heteroarylalkenyl, heteroarylalkoxy, heteroarylealkyl, heteroaryloxyalkyl, heterocycle, heterocyclealkenyl, heterocyclealkoxy, heterocyclealkyl, heterocycleoxyalkyl, hydroxy, hydroxyalkoxy, hydroxyalkyl, $(NR_CR_D)$alkenyl, $(NR_CR_D)$alkoxy, $(NR_CR_D)$alkyl, $(NR_CR_D)$alkynyl, $(NR_CR_D)$carbonylalkenyl, and $(NR_CR_D)$carbonylalkyl;

$R_3$ and $R_4$ are independently selected from the group consisting of hydrogen, alkoxy, alkoxyalkoxy, alkoxyalkyl, alkyl, arylalkyl, aryloxy, aryloxyalkyl, halo, haloalkoxy, haloalkyl, heteroarylalkenyl, heteroarylalkoxy, heteroarylealkyl, heteroaryloxyalkyl, heterocycle, heterocyclealkenyl, heterocyclealkoxy, heterocyclealkyl, heterocycleoxyalkyl, hydroxy, hydroxyalkoxy, hydroxyalkyl, $(NR_CR_D)$alkenyl, $(NR_CR_D)$alkoxy, $(NR_CR_D)$alkyl, $(NR_CR_D)$alkynyl, $(NR_CR_D)$carbonylalkenyl, and $(NR_CR_D)$carbonylalkyl;

$R_5$, $R_6$, and $R_7$ are independently selected from the group consisting of hydrogen, alkoxy, alkoxyalkoxy, alkyl, halo, haloalkoxy, haloalkyl, hydroxy, and —$NR_ER_F$;

L is selected from the group consisting of $(CH_2)_mN(R_{10})C(O)N(R_{11})(CH_2)_n$ and $CH_2C(O)NR_{10}$, wherein wherein each group is drawn with its left end attached to the phenyl ring substituted with $R_5$, $R_6$, and $R_7$;

m and n are independently 0 or 1;

$R_{10}$ and $R_{11}$, are independently selected from the group consising of hydrogen and alkyl;

$R_{12}$, $R_{13}$, and $R_{14}$ are independently selected from the group consisting of hydrogen, alkenyl, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylthio, alkylthioalkyl, alkynyl, carboxy, carboxyalkyl, cyano, cyanoalkyl, ethylenedioxy, formyl, haloalkoxy, haloalkyl, halogen, hydroxy, hydroxyalkyl, mercapto, methylenedioxy, nitro, —$NR_GR_H$, $(NR_GR_H)$carbonyl, and $(NR_GR_H)$sulfonyl;

$R_A$ and $R_B$ are independently selected from the group consisting of hydrogen and alkyl;

$R_C$ and $R_D$ are independently selected from the group consisting of hydrogen, alkenyl, alkyl, alkylcarbonyl, alkylsulfonyl, aryl, arylalkyl, arylcarbonyl, arylsulfonyl, haloalkylsulfonyl, cycloalkyl, cycloalkylalkyl, heteroaryl, heteroarylalkyl, heteroarylsulfonyl, heterocycle, heterocyclealkyl, and heterocyclesulfonyl;

$R_E$ and $R_F$ are independently selected from the group consisting of hydrogen, alkyl, and alkylcarbonyl; and $R_G$ and $R_H$ are independently selected from the group consisting of hydrogen, alkyl, alkylcarbonyl, aryl, and arylalkyl.

In another embodiment, the present invention provides a compound of formula (II) wherein $X_2$ is N; $X_3$ is $CR_3$; $X_4$ is $CR_4$; and L, $R_1$, $R_3$, $R_4$, $R_5$, $R_6$, $R_7$, $R_{12}$, $R_{13}$, and $R_{14}$ are as defined in formula (I).

In another embodiment, the present invention provides a compound of formula (II) wherein $X_2$ is N; $X_3$ is $CR_3$; $X_4$ is $CR_4$; $R_1$ is selected from the group consisting of hydrogen and methyl; $R_3$, $R_4$, $R_5$, $R_6$, and $R_7$ are hydrogen; $R_{12}$, $R_{13}$, and $R_{14}$ are independently selected from the group consisting of hydrogen, alkoxy, alkyl, haloalkyl, and halogen; L is $(CH_2)_mN(R_{10})C(O)N(R_{11})(CH_2)_n$; m is 0; n is 0; and $R_{10}$ and $R_{11}$ are hydrogen.

In another embodiment, the present invention provides a compound of formula (II) wherein $X_2$ is $CR_2$; $X_3$ is N; $X_4$ is $CR_4$; and L, $R_1$, $R_2$, $R_4$, $R_5$, $R_6$, $R_7$, $R_{12}$, $R_{13}$, and $R_{14}$ are as defined in formula (II).

In another embodiment, the present invention provides a compound of formula (II) wherein $X_2$ is $CR_2$; $X_3$ is N; $X_4$ is $CR_4$; $R_1$ is selected from the group consisting of hydrogen and methyl; $R_2$, $R_4$, $R_5$, $R_6$, and $R_7$ are hydrogen; $R_{12}$, $R_{13}$, and $R_{14}$ are independently selected from the group consisting of hydrogen, alkoxy, alkyl, haloalkyl, and halogen; L is $(CH_2)_mN(R_{10})C(O)N(R_{11})(CH_2)_n$; m is 0; n is 0; and $R_{10}$ and $R_{11}$, are hydrogen.

In another embodiment, the present invention provides a compound of formula (II) wherein $X_2$ is $CR_2$; $X_3$ is $CR_3$; $X_4$ is N; and L, $R_1$, $R_2$, $R_3$, $R_5$, $R_6$, $R_7$, $R_{12}$, $R_{13}$, and $R_{14}$ are as defined in formula (II).

In another embodiment, the present invention provides a compound of formula (II) wherein $X_2$ is $CR_2$; $X_3$ is $CR_3$; $X_4$ is N; $R_1$ is selected from the group consisting of hydrogen and methyl; $R_2$, $R_3$, $R_5$, $R_6$, and $R_7$ are hydrogen; $R_{12}$, $R_{13}$, and $R_{14}$ are independently selected from the group consisting of hydrogen, alkoxy, alkyl, haloalkyl, and halogen; L is $(CH_2)_mN(R_{10})C(O)N(R_{11})(CH_2)_n$; m is 0; n is 0; and $R_{10}$ and $R_{11}$ are hydrogen.

All patents, patent applications, and literature references cited in the specification are herein incorporated by reference in their entirety. In the case of inconsistencies, the present disclosure, including definitions, will prevail.

As used throughout this specification and the appended claims, the following terms have the following meanings:

The term "alkenyl" as used herein, means a straight or branched chain hydrocarbon containing from 2 to 10 carbons and containing at least one carbon-carbon double bond formed by the removal of two hydrogens.

The term "alkoxy" as used herein, means an alkyl group, as defined herein, appended to the parent molecular moiety through an oxygen atom.

The term "alkoxyalkoxy" as used herein, means an alkoxy group, as defined herein, appended to the parent molecular moiety through another alkoxy group, as defined herein.

The term "alkoxyalkyl" as used herein, means an alkoxy group, as defined herein, appended to the parent molecular moiety through an alkyl group, as defined herein.

The term "alkoxycarbonyl" as used herein, means an alkoxy group, as defined herein, appended to the parent molecular moiety through a carbonyl group, as defined herein.

The term "alkoxycarbonylalkyl" as used herein, means an alkoxycarbonyl group, as defined herein, appended to the parent molecular moiety through an alkyl group, as defined herein.

The term "alkoxysulfonyl" as used herein, means an alkoxy group, as defined herein, appended appended to the parent molecular moiety through a sulfonyl group, as defined herein.

The term "alkyl" as used herein, means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylcarbonyl" as used herein, means an alkyl group, as defined herein, appended to the parent molecular moiety through a carbonyl group, as defined herein.

The term "alkylcarbonylalkyl" as used herein, means an alkylcarbonyl group, as defined herein, appended to the parent molecular moiety through an alkyl group, as defined herein.

The term "alkylcarbonyloxy" as used herein, means an alkylcarbonyl group, as defined herein, appended to the parent molecular moiety through an oxygen atom.

The term "alkylsulfonyl" as used herein, means an alkyl group, as defined herein, appended to the parent molecular moiety through a sulfonyl group, as defined herein.

The term "alkylthio" as used herein, means an alkyl group, as defined herein, appended to the parent molecular moiety through a sulfur atom.

The term "alkylthioalkyl" as used herein, means an alkylthio group, as defined herein, appended to the parent molecular moiety through an alkyl group, as defined herein.

The term "alkynyl" as used herein, means a straight or branched chain hydrocarbon group containing from 2 to 10 carbon atoms and containing at least one carbon-carbon triple bond.

The term "aryl," as used herein, means a phenyl group or a naphthyl group.

The aryl groups of the present invention can be optionally substituted with one, two, three, four, or five substituents independently selected from the group consisting of alkenyl, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylthio, alkylthioalkyl, alkynyl, carboxy, carboxyalkyl, cyano, cyanoalkyl, ethylenedioxy, formyl, haloalkoxy, haloalkyl, halogen, hydroxy, hydroxyalkyl, mercapto, methylenedioxy, nitro, —NR$_G$R$_H$, (NR$_G$R$_H$)carbonyl, and (NR$_G$R$_H$)sulfonyl.

The term "arylalkyl" as used herein, means an aryl group, as defined herein, appended to the parent molecular moiety through an alkyl group, as defined herein.

The term "arylcarbonyl" as used herein, means an aryl group, as defined herein, appended to the parent molecular moiety through a carbonyl group, as defined herein.

The term "aryloxy" as used herein, means an aryl group, as defined herein, appended to the parent molecular moiety through an oxygen atom.

The term "aryloxyalkyl" as used herein, means an aryloxy group, as defined herein, appended to the parent molecular moiety through an alkyl group, as defined herein.

The term "arylsulfonyl" as used herein, means an aryl group, as defined herein, appended to the parent molecular moiety through a sulfonyl group, as defined herein.

The term "carbonyl" as used herein, means a —C(O)— group.

The term "carboxy" as used herein, means a —CO$_2$H group.

The term "carboxyalkyl" as used herein, means a carboxy group, as defined herein, appended to the parent molecular moiety through an alkyl group, as defined herein.

The term "cyano" as used herein, means a —CN group.

The term "cyanoalkyl" as used herein, means a cyano group, as defined herein, appended to the parent molecular moiety through an alkyl group, as defined herein.

The term "cycloalkyl" as used herein, means a saturated cyclic hydrocarbon group containing from 3 to 8 carbons, examples of cycloalkyl include cyclopropyl, cyclobutyl, cyclopentyl, cyclohexyl, cycloheptyl, and cyclooctyl.

The cycoalkyl groups of the present invention are optionally substituted with 1, 2, 3, or 4 substituents selected from alkenyl, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylthio, alkylthioalkyl, alkynyl, carboxy, carboxyalkyl, cyano, cyanoalkyl, formyl, haloalkoxy, haloalkyl, halogen, hydroxy, hydroxyalkyl, mercapto, oxo, —NR$_G$R$_H$, and (NR$_G$R$_H$)carbonyl.

The term "cycloalkylalkyl" as used herein, means a cycloalkyl group, as defined herein, appended to the parent molecular moiety through an alkyl group, as defined herein. Representative examples of cycloalkylalkyl include, but are not limited to, cyclopropylmethyl, 2-cyclobutylethyl, cyclopentylmethyl, cyclohexylmethyl, and 4-cycloheptylbutyl.

The term "ethylenedioxy" as used herein, means a —O(CH$_2$)$_2$O— group wherein the oxygen atoms of the ethylenedioxy group are attached to the parent molecular moiety through one carbon atom forming a 5 membered ring or the oxygen atoms of the ethylenedioxy group are attached to the parent molecular moiety through two adjacent carbon atoms forming a six membered ring.

The term "formyl" as used herein, means a —C(O)H group.

The term "halo" or "halogen" as used herein, means —Cl, —Br, —I or —F.

The term "haloalkoxy" as used herein, means at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, and pentafluoroethoxy.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "haloalkylsulfonyl" as used herein, means a haloalkyl group, as defined herein, appended to the parent molecular moiety through a sulfonyl group, as defined herein.

The term "heteroaryl," as used herein, means a monocyclic heteroaryl ring or a bicyclic heteroaryl ring. The monocyclic heteroaryl ring is a 5 or 6 membered ring. The 5 membered ring has two double bonds and contains one, two, three or four heteroatoms independently selected from the group consisting of N, O, and S. The 6 membered ring has three double bonds and contains one, two, three or four heteroatoms independently selected from the group consisting of N, O, and S. The bicyclic heteroaryl ring consists of the 5 or 6 membered heteroaryl ring fused to a phenyl group or the 5 or 6 membered heteroaryl ring fused to another 5 or 6 membered heteroaryl ring. Nitrogen heteroatoms contained within the heteroaryl may be optionally oxidized to the N-oxide or optionally protected with a nitrogen protecting group known to those of skill in the art. The heteroaryl is connected to the parent molecular moiety through any carbon atom or any nitrogen atom contained within the heteroaryl. Representative examples of heteroaryl include, but are not limited to, benzothienyl, benzoxadiazolyl, cinnolinyl, furopyridinyl, furyl, imidazolyl, indazolyl, indolyl, isoxazolyl, isoquinolinyl, isothiazolyl, naphthyridinyl, oxadiazolyl, oxazolyl, pyridinyl, pyridazinyl, pyrimidinyl, pyrazinyl, pyrazolyl, pyrrolyl, pyridinium N-oxide, quinolinyl, tetrazolyl, thiadiazolyl, thiazolyl, thienopyridinyl, thienyl, triazolyl, and triazinyl.

The heteroaryl groups of the present invention are substituted with 0, 1, 2, 3, or 4 substituents independently selected from alkenyl, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylthio, alkylthioalkyl, alkynyl, carboxy, carboxyalkyl, cyano, cyanoalkyl, ethylenedioxy, formyl, haloalkoxy, haloalkyl, halogen, hydroxy, hydroxyalkyl, mercapto, methylenedioxy, nitro, —NR$_G$R$_H$, (NR$_G$R$_H$)carbonyl, and (NR$_G$R$_H$)sulfonyl. Heteroaryl groups of the present invention that are substituted may be present as tautomers. The present invention encompasses all tautomers including non-aromatic tautomers.

The term "heteroarylalkenyl" as used herein, means a heteroaryl, as defined herein, appended to the parent molecular moiety through an alkenyl group, as defined herein.

The term "heteroarylalkoxy" as used herein, means a heteroaryl group, as defined herein, appended to the parent molecular moiety through an alkoxy group, as defined herein.

The term "heteroarylalkyl" as used herein, means a heteroaryl, as defined herein, appended to the parent molecular moiety through an alkyl group, as defined herein.

The term "heteroarylsulfonyl" as used herein, means a heteroaryl, as defined herein, appended to the parent molecular moiety through a sulfonyl group, as defined herein.

The term "heterocycle" or "heterocyclic" as used herein, means a monocyclic heterocyclic ring or a bicyclic heterocyclic ring. The monocyclic heterocyclic ring consists of a 3, 4, 5, 6 or 7 membered ring containing at least one heteroatom independently selected from oxygen, nitrogen and sulfur. The 3 or 4 membered ring contains 1 heteroatom selected from the group consisting of O, N and S. The 5 membered ring contains zero or one double bond and one, two or three heteroatoms selected from the group consisting of O, N and S. The 6 or 7 membered ring contains zero, one or two double bonds and one, two or three heteroatoms selected from the group consisting of O, N and S. Representative examples of the monocyclic heterocyclic ring include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocyclic ring consists of the monocyclic heterocyclic ring fused to a phenyl group or the monocyclic heterocyclic ring fused to a cycloalkyl group or the monocyclic heterocyclic ring fused to another monocyclic heterocyclic ring.

The heterocycles of this invention are substituted with 0, 1, 2, or 3 substituents independently selected from alkenyl, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylthio, alkylthioalkyl, alkynyl, carboxy, carboxyalkyl, cyano, cyanoalkyl, ethylenedioxy, formyl, haloalkoxy, haloalkyl, halogen, hydroxy, hydroxyalkyl, mercapto, methylenedioxy, nitro, oxo, —NR$_G$R$_H$, and (NR$_G$R$_H$)carbonyl.

The term "heterocyclealkenyl" as used herein, means a heterocycle group, as defined herein, appended to the parent molecular moiety through an alkenyl group, as defined herein.

The term "heterocyclealkoxy" as used herein, means a heterocycle group, as defined herein, appended to the parent molecular moiety through an alkoxy group, as defined herein.

The term "heterocyclealkyl" as used herein, means a heterocycle, as defined herein, appended to the parent molecular moiety through an alkyl group, as defined herein.

The term "heterocyclesulfonyl" as used herein, means a heterocycle, as defined herein, appended to the parent molecular moiety through a sulfonyl group, as defined herein.

The term "heterocycleoxy" as used herein, means a heterocycle group, as defined herein, appended to the parent molecular moiety through an oxygen atom.

The term "heterocycleoxyalkyl" as used herein, means a heterocycleoxy group, as defined herein, appended to the parent molecular moiety through an alkyl group, as defined herein.

The term "hydroxy" as used herein, means an —OH group.

The term "hydroxyalkoxy" as used herein, means at least one hydroxy group, as defined herein, is appended to the parent molecular moiety through an alkoxy group, as defined herein.

The term "hydroxyalkyl" as used herein, means at least one hydroxy group, as defined herein, is appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "mercapto" as used herein, means a —SH group.

The term "methylenedioxy" as used herein, means a —OCH$_2$O— group wherein the oxygen atoms of the methylenedioxy are attached to the parent molecular moiety through two adjacent carbon atoms.

The term "nitro" as used herein, means a —NO$_2$ group.

The term "—NR$_A$R$_B$" as used herein, means two groups, R$_A$ and R$_B$, which are appended to the parent molecular moiety through a nitrogen atom. R$_A$ and R$_B$ are each independently hydrogen, alkyl, aryl, and arylalkyl. Representative examples of NR$_A$R$_B$ include, but are not limited to, amino, benzylamine, phenylamine, methylamino, dimethylamino, diethylamino, and ethylmethylamino.

The term "(NR$_A$R$_B$)carbonyl" as used herein, means a —NR$_A$R$_B$ group, as defined herein, appended to the parent molecular moiety through a carbonyl group, as defined herein. Representative examples of (NR$_A$R$_B$)carbonyl include, but are not limited to, aminocarbonyl, (methylamino)carbonyl, (dimethylamino)carbonyl, and (ethylmethylamino)carbonyl.

The term "(NR$_A$R$_B$)sulfonyl" as used herein, means a —NR$_A$R$_B$ group, as defined herein, appended to the parent molecular moiety through a sulfonyl group, as defined herein.

The term "(NR$_A$R$_B$)sulfonylalkyl" as used herein, means a (NR$_A$R$_B$)sulfonyl group, as defined herein, appended to the parent molecular moiety through an alkyl group, as defined herein.

The term "—NR$_C$R$_D$" as used herein, means two groups, R$_C$ and R$_D$, which are appended to the parent molecular moiety through a nitrogen atom. R$_C$ and R$_D$ are each independently hydrogen, alkenyl, alkyl, alkylcarbonyl, alkylsulfonyl, aryl, arylalkyl, arylcarbonyl, arylsulfonyl, haloalkylsulfonyl, cycloalkyl, cycloalkylalkyl, heteroaryl, heteroarylalkyl, heteroarylsulfonyl, heterocycle, heterocyclealkyl, and heterocyclesulfonyl.

The term "(NR$_C$R$_D$)alkenyl" as used herein, means a —NR$_C$R$_D$ group, as defined herein, appended to the parent molecular moiety through an alkenyl group, as defined herein.

The term "(NR$_C$R$_D$)alkoxy" as used herein, means a —NR$_C$R$_D$ group, as defined herein, appended to the parent molecular moiety through an alkoxy group, as defined herein.

The term "(NR$_C$R$_D$)alkyl" as used herein, means a —NR$_C$R$_D$ group, as defined herein, appended to the parent molecular moiety through an alkyl group, as defined herein.

The term "(NR$_C$R$_D$)alkynyl" as used herein, means a —NR$_C$R$_D$ group, as defined herein, appended to the parent molecular moiety through an alkynyl group, as defined herein.

The term "(NR$_C$R$_D$)carbonyl" as used herein, means a —NR$_C$R$_D$ group, as defined herein, appended to the parent molecular moiety through a carbonyl group, as defined herein.

The term "(NR$_C$R$_D$)carbonylalkenyl" as used herein, means a (NR$_C$R$_D$)carbonyl group, as defined herein, appended to the parent molecular moiety through an alkenyl group, as defined herein.

The term "(NR$_C$R$_D$)carbonylalkyl" as used herein, means a (NR$_C$R$_D$)carbonyl group, as defined herein, appended to the parent molecular moiety through an alkyl group, as defined herein.

The term "—NR$_E$R$_F$" as used herein, means two groups, R$_E$ and R$_F$, which are appended to the parent molecular moiety through a nitrogen atom. R$_E$ and R$_F$ are independently hydrogen, alkyl, and alkylcarbonyl.

The term "—NR$_G$R$_H$" as used herein, means two groups, R$_G$ and R$_H$, which are appended to the parent molecular moiety through a nitrogen atom. R$_G$ and R$_H$ are independently hydrogen, alkyl, alkylcarbonyl, aryl, and arylalkyl.

The term "(NR$_G$R$_H$)carbonyl" as used herein, means a —NR$_G$R$_H$ group, as defined herein, appended to the parent molecular moiety through a carbonyl group, as defined herein. Representative examples of (NR$_G$R$_H$)carbonyl include, but are not limited to, aminocarbonyl, (methylamino)carbonyl, (dimethylamino)carbonyl, (diethylamino)carbonyl, and (ethylmethylamino)carbonyl.

The term "(NR$_G$R$_H$)sulfonyl" as used herein, means a —NR$_G$R$_H$ group, as defined herein, appended to the parent molecular moiety through a sulfonyl group, as defined herein.

The term "oxo" as used herein, means a =O moiety.

The term "sulfonyl" as used herein, means a —SO$_2$— group.

The compounds of the present invention can exist as therapeutically acceptable salts. The term "therapeutically acceptable salt," as used herein, represents salts or zwitterionic forms of the compounds of the present invention which are water or oil-soluble or dispersible, which are suitable for treatment of diseases without undue toxicity, irritation, and allergic response; which are commensurate with a reasonable benefit/risk ratio, and which are effective for their intended use. The salts can be prepared during the final isolation and purification of the compounds or separately by reacting an —NR$^a$R$^b$ group with a suitable acid. Representative acid addition salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, fulmarate, hydrochloride, hydrobromide, hydroiodide, 2-hydroxyethansulfonate, lactate, maleate, mesitylenesulfonate, methanesulfonate, naphthylenesulfonate, nicotinate, 2-naphthalenesulfonate, oxalate, pamoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Also, amine groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric.

The present compounds can also exist as therapeutically acceptable prodrugs. The term "therapeutically acceptable prodrug," refers to those prodrugs or zwitterions which are suitable for use in contact with the tissues of patients without undue toxicity, irritation, and allergic response, are commensurate with a reasonable benefit/risk ratio, and are effective for their intended use. The term "prodrug," refers to compounds which are rapidly transformed in vivo to parent compounds of formula (I) or (II) for example, by hydrolysis in blood.

When it is possible that, for use in therapy, therapeutically effective amounts of a compound of formula (I) or (II), as well as therapeutically acceptable salts thereof, may be administered as the raw chemical, it is possible to present the active ingredient as a pharmaceutical composition. Accordingly, the invention further provides pharmaceutical compositions, which include therapeutically effective amounts of compounds of formula (I) or (II), or therapeutically acceptable salts thereof, and one or more pharmaceutically acceptable carriers, diluents, or excipients. The compounds of formula (I) and (II) and therapeutically acceptable salts thereof are as described above. The carrier(s), diluent(s), or excipient(s) must be acceptable in the sense of being compatible with the other ingredients of the formulation and not deleterious to the recepient thereof. In accordance with another aspect of the invention there is also provided a process for the preparation of a pharmaceutical formulation including admixing a compound of formula (I) or (II), or a therapeutically acceptable salt thereof, with one or more pharmaceutically acceptable carriers, diluents, or excipients.

Pharmaceutical formulations may be presented in unit dose forms containing a predetermined amount of active ingredient per unit dose. Such a unit may contain, for example, 0.5 mg to 1 g, preferably 1 mg to 700 mg, more preferably 5 mg to 100 mg of a compound of formula (I) or (II), depending on the condition being treated, the severity of the condition, the time of administration, the route of administration, the rate of excretion of the compound employed, the duration of treatment, and the age, gender, weight, and condition of the patient, or pharmaceutical formulations may be presented in unit dose forms containing a predetermined amount of an active ingredient per dose. Preferred unit dosage formulations are those containing a daily dose or sub-dose, as herein above recited, or an appropriate fraction thereof, of an active ingredient. Furthermore, such pharmaceutical formulations may be prepared by any of the methods well known in the pharmacy art.

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intramuscular, intravenous, or intradermal) route. Such formulations may be prepared by any method known in the art of pharmacy, for example by bringing into association the active ingredient with the carrier(s) or excipient(s). In addition, compounds of the present invention can be administered using conventional drug delivery technology, for example, intra-arterial stents.

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by cumminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an altenative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solutions, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxy ethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of formula (I) and (II), and therapeutically acceptable salts thereof, can also be administered in the form of liposome delivery systems, such as small unilamellar vesicles, large unilamellar vesicles, and multilamellar vesicles. Liposomes can be formed from a variety of phospholipids, such as cholesterol, stearylamine, or phophatidylcholines.

The compounds of formula (I) and (II), and therapeutically acceptable salts thereof, may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in oil base.

Pharmaceutical formulations adapted for topical administrations to the eye include eye drops wherein the active ingredient is dissolved or suspended in a suitable carrier, especially an aqueous solvent Pharmaceutical formulations adapted for topical administration in the mouth include lozenges, pastilles, and mouth washes.

Pharmaceutical formulations adapted for rectal administration may be presented as suppositories or as enemas.

Pharmaceutical formulations adapted for nasal administration wherein the carrier is a solid include a course powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

A therapeutically effective amount of a compound of the present invention will depend upon a number of factors including, for example, the age and weight of the animal, the precise condition requiring treatment and its severity, the nature of the formulation, and the route of administration, and will ultimately be at the discretion of the attendant physician or veterinarian. However, an effective amount of a compound of formula (I) or (II) for the treatment of neoplastic growth, for example colon or breast carcinoma, will generally be in the range of 0.1 to 100 mg/kg body weight of recipient (mammal) per day and more usually in the range of 1 to 10 mg/kg body weight per day.

The compounds of the present invention and therapeutically acceptable salts thereof, may be employed alone or in combination with other therapeutic agents for the treatment of the above-mentioned conditions. In particular, in anti-cancer therapy, combination with other chemotherapeutic, hormonal, or antibody agents is envisaged as well as combination with surgical therapy and radiotherapy. Combination therapies according to the present invention thus comprise the administration of at least one compound of formula (I) or (II), or a therapeutically acceptable salt thereof, and the use of at least one other cancer treatment method. Preferably, combination therapies according to the present invention comprise the administration of at least one other pharmaceutically active agent, preferably an anti-neoplastic agent. The compound(s) of formula (I) or (II) and the other pharmaceutically active agent(s) may be administered together or separately and when administered separately this may occur simultaneously or sequentially in any order. The amounts of the compound(s) of formula (I) or (II) and the other pharmaceutically active agent(s) and the relative timings of administration will be selected in order to achieve the desired combined therapeutic effect.

The compounds of formula (I) or (II), or therapeutically acceptable salts thereof, and at least one additional cancer treatment therapy may be employed in combination concomitantly or sequentially in any therapeutically appropriate combination with such other anti-cancer therapies. In one embodiment, the other anti-cancer therapy is at least one additional chemotherapeutic therapy including administration of at least one anti-neoplastic agent. The administration in combination of a compound of formula (I) or (II), or therapeutically acceptable salts thereof, with other anti-neoplastic agents may be in combination in accordance with the invention by administration concomitantly in (1) a unitary pharmaceutical composition including both compounds or (2) separate pharmaceutical compositions each including one of the compounds. Alternatively, the combination may be administered separately in a sequential manner wherein one anti-neoplastic agent is administered first and the other second or vice versa. Such sequential administration may be close in time or remote in time.

Anti-neoplastic agents may induce anti-neoplastic effects in a cell-cycle specific manner, i.e., are phase specific and act at a specific phase of the cell cycle, or bind DNA and act in a non cell-cycle specific manner, i.e., are non-cell cycle specific and operate by other mechanisms.

Anti-neoplastic agents useful in combination with the compounds and salts of formula (I) or (II) include the following:

(1) cell cycle specific anti-neoplastic agents including, but not limited to, diterpenoids such as paclitaxel and its analog docetaxel; vinca alkaloids such as vinblastine, vincristine, vindesine, and vinorelbine; epipodophyllotoxins such as etoposide and teniposide; fluoropyrimidines such as 5-fluorouracil and fluorodeoxyuridine; antimetabolites such as allopurinol, fludurabine, methotrexate, cladrabine, cytarabine, mercaptopurine, and thioguanine; and camptothecins such as 9-amino camptothecin, irinotecan, topotecan, CPT-11, and the various optical forms of 7-(-4-methylpiperazino-methylene)-10,11-ethylenedioxy-20-camptothecin;

(2) cytotoxic chemotherapeutic agents including, but not limited to, alkylating agents such as melphalan, chlorambucil, cyclophosphamide, mechlorethamine, hexamethylmelamine, busulfan, carmustine, lomustine, and dacarbazine; anti-tumor antibiotics such as doxorubicin, daunomycin, epirubicin, idarubicin, mitomycin-C, dacttainomycin, and mithramycin; and platinum coordination complexes such as cisplatin, carboplatin, and oxaliplatin; and (3) other chemotherapeutic agents including, but not limited to, anti-estrogens such as tomixefen, toremifene, raloxifene, droloxifene, and iodoxyfene; progesterogens such as megastrol acetate; aromatase inhibitors such as anastrozole, letrazole, vorazole, and exemestane; antiandrogens such as flutamide, nilutamide, bicalutamide, and cyproterone acetate; LHRH agonists and antagonists such as goserelin acetate and luprolide, testosterone 5α-dihydroreductase inhibitors such as finasteride; metallopreteinase inhibitors such as marimastat; antiprogestogens; urokinase plasminogen activator receptor function inhibitors; growth factor function inhibitors such as inhibitors of the functions of hepatocyte growth factor, erb-B2, erb-B4, epidermal growth factor receptor (EGFR), platelet derived growth factor receptor (PDGFR), vascular endothelial growth factor receptor (VEGFR and TIE-2 (other than those VEGFR and TIE-2 inhibitors described in the present invention)); and other tyrosine kinase inhibitors such as inhibitors of CDK2 and CDK4 inhibitors.

Determination of Biological Activity

The in vitro potency of compounds in inhibiting these protein kinases may be determined by the procedures detailed below.

The potency of compounds can be determined by the amount of inhibition of the phosphorylation of an exogenous substrate (e.g., synthetic peptide (Z. Songyang et al., Nature. 373:536-539) by a test compound relative to control.

All reagents are reagent grade or better and are available commercially unless otherwise indicated.

KDR Tyrosine Kinase Production Using Baculovirus System:

The coding sequence for the human KDR intra-cellular domain (aa789-1354) was generated through PCR using cDNAs isolated from HUVEC cells. A poly-His6 sequence was introduced at the N-terminus of this protein as well. This fragment was cloned into transfection vector p VL1393 at the Xba 1 and Not 1 site. Recombinant baculovirus (BV) was generated through co-transfection using the BaculoGold Transfection reagent (PharMingen). Recombinant BV was plaque purified and verified through Western analysis. For protein production, SF-9 cells were grown in SF-900-II medium at 2×106/ml, and were infected at 0.5 plaque forming units per cell (MOI). Cells were harvested at 48 hours post infection.

Purification of KDR

SF-9 cells expressing $(His)_6KDR(aa789-1354)$ were lysed by adding 50 ml of Triton X-100 lysis buffer (20 mM Tris, pH 8.0, 137 mM NaCl, 10% glycerol, 1% Triton X-100, 1 mM PMSF, 10 µg/ml aprotinin, 1 µg/ml leupeptin) to the cell pellet from 1L of cell culture. The lysate was centrifuged at 19,000 rpm in a Sorval SS-34 rotor for 30 min at 4° C. The cell lysate was applied to a 5 ml $NiCl_2$ chelating sepharose column, equilibrated with 50 mM HEPES, pH7.5, 0.3 M NaCl. KDR was eluted using the same buffer containing 0.25 M imidazole. Column fractions were analyzed using SDS-PAGE and an ELISA assay (below) which measures kinase activity. The purified KDR was exchanged into 25 mM HEPES, pH7.5, 25 mM NaCl, 5 mM DTT buffer and stored at −80° C.

Compounds of the present invention inhibited KDR at $IC_{50s}$ between about 0.001 µM and about 1.0 µM.

Human Tie-2 Kinase Production and Purification

The coding sequence for the human Tie-2 intra-cellular domain (aa775-1124) was generated through PCR using cDNAs isolated from human placenta as a template. A poly-$His_6$ sequence was introduced at the N-terminus and this construct was cloned into transfection vector pVL 1939 at the Xba 1 and Not 1 site. Recombinant BV was generated through co-transfection using the BaculoGold Transfection reagent (PharMingen). Recombinant BV was plaque purified and verified through Western analysis. For protein production, SF-9 insect cells were grown in SF-900-II medium at 2×106/ml, and were infected at MOI of 0.5. Purification of the His-tagged kinase used in screening was analogous to that described for KDR.

Human Flt-1 Tyrosine Kinase Production and Purification

The baculoviral expression vector pVL1393 (Phar Mingen, Los Angeles, Calif.) was used. A nucleotide sequence encoding poly-His6 was placed 5' to the nucleotide region encoding the entire intracellular kinase domain of human Flt-1 (amino acids 786-1338). The nucleotide sequence encoding the kinase domain was generated through PCR using cDNA libraries isolated from HUVEC cells. The histidine residues enabled affinity purification of the protein as a manner analogous to that for KDR and ZAP70. SF-9 insect cells were infected at a 0.5 multiplicity and harvested 48 hours post infection.

EGFR Tyrosine Kinase Source

EGFR was purchased from Sigma (500 units/50 µL) and the EGF ligand was acquired from Oncogene Research Products/Calbiochem.

Protein Kinase Source

Lck, Fyn, Src, Blk, Csk, and Lyn, and truncated forms thereof may be commercially obtained (e.g., from Upstate Biotechnology Inc. and Santa Cruz Biotechnology Inc.) or purified from known natural or recombinant sources using conventional methods.

Homogenous Time-resolved Fluorescence (HTRF) in Vitro Kinase Assay (Mathis, G., HTRF (R) Technology. J Biomol Screen, 1999. 4(6): p. 309-314; Alfred J. Kolb, Paul V. Kaplita, David J. Hayes, Young-Whan Park, Christine Pernell, John S. Major and Gérard Mathis, Drug Discovery Today, 1998, 3, 333-342.):

For example, purified enzyme was mixed with 4 µM N-biotinylated substrate (e.g., poly($Glu_4Tyr$)) and various concentrations of inhibitor in reaction buffer (50 mM HEPES, pH 7.1, 10 mM $MgCl_2$, 2 mM $MnCl_2$, 0.1% BSA and 1 mM DTT, 40 µL final volume). The kinase reaction was initiated by addition of ATP (1 mM final conc.) in a black 96-well plate (Packard). After 30-60 minutes incubation at room temperature, the reaction was quenched by addition of a buffered EDTA solution (final approximate concentrations: 30 mM EDTA, 0.1% BSA, 0.1% Triton X-100 and 0.24M KF) and a solution of revelation agents (to give 0.084 ng/well streptavidin-XL-665 (Cis-Bio) and 6.5 ng/well antiphsophotyrosine mAb PT66-K Europium kryptate) was added to the reaction mixture. The quenched reaction was allowed to stand at room temperature for 3 hour and then read in a time-resolved fluorescence detector (Discovery, Packard) at 620 nm and 665 nm simultaneously. A 337 nm nitrogen laser was used for excitation. The ratio between the signal of 620 nm and 665 nm was used in the calculation of the $IC_{50}$.

More specific details for the various enzymes are included below in Table 1:

TABLE 1

| | | | | | HTRF ASSAYS | | | | |
|---|---|---|---|---|---|---|---|---|---|
| Enzyme | Construct | MW (kD) | Enz. Reaction Conc. (ng/well) | Assay Buffer | Substrate | Peptide Substrate Conc. (µM) | ATP Conc. (mM) | DMSO Conc. (%) | Reaction Time (min) |
| Lck (Truncated) | 62-509 | 52 | 2.1 | MOPSO | bio-LCK peptide | 4 | 1 | 5 | 60 |
| Src (UBI) | NA | 60 | 0.15 U/well | MOPSO | bio-LCK peptide | 4 | 1 | 5 | 60 |
| Lyn | His6-Tag | 52 | 0.5 | MOPSO | bio-LCK peptide | 4 | 1 | 5 | 60 |
| Fyn (Catalytic Domain) | His6-Tag (257-534) | 34 | 0.15 | MOPSO | bio-LCK peptide | 4 | 1 | 5 | 60 |
| Csk | His6-Tag | 50 | 0.33 | MOPSO | bio-PGT | 4 | 1 | 5 | 10 |
| Lck (Catalytic Domain) | His6-Tag | 35 | 1 | MOPSO | bio-LCK peptide | 4 | 1 | 5 | 60 |
| Blk (Catalytic Domain) | His6-Tag | 60 | 0.15 | MOPSO | bio-LCK peptide | 4 | 1 | 5 | 60 |
| KDR | His6-KDR 789-1354 | 63 | 7 | HEPES | bio-FGFR peptide | 4 | 1 | 5 | 60 |

TABLE 1-continued

| | | | HTRF ASSAYS | | | | | | |
|---|---|---|---|---|---|---|---|---|---|
| Enzyme | Construct | MW (kD) | Enz. Reaction Conc. (ng/well) | Assay Buffer | Substrate | Peptide Substrate Conc. (µM) | ATP Conc. (mM) | DMSO Conc. (%) | Reaction Time (min) |
| Tie2 | His6-Tag | 40 | 12.6 | HEPES | bio-PGT | 10 ng/well | 1 | 5 | 10 |
| cKIT | GST-Fusion | 70 | 4* | HEPES | bio-FGFR peptide | 0.5* | 1 | 5 | 60 |
| Flt1 | His6-Tag | 65 | | HEPES | bio-FGFR peptide | 4 | 1 | 5 | 60 |
| CSF-1r | M-His(6)-CSF-IR Q547-C972 | 50 | 10 | HEPES | bio-Lck peptide | 4 | 1 | 5 | 60 |

Substrates

Bio-FGFR peptide means biotin-(6-aminohexanoic acid)-FGFR peptide wherein the FGFR peptide is as described in Z. Songyang et. al., Nature, 373:536-539 (1995) except that alanine amide was added to the carboxy end.

Bio-LCK peptide means biotin-(6-aminohexanoic acid)-Lck peptide wherein the Lck peptide is as described in Z. Songyang et. al., Nature, 373:536-539 (1995) except that glycine-alanine was added to the amino end, valine was substituted for alanine at the +2 position, and alanine was truncated.

One well contains a total of 40 µL reagents.

Compounds of the present invention have therapeutic utility in the treatment of diseases involving both identified, including those not mentioned herein, and as yet unidentified protein tyrosine kinases which are inhibited by compounds of the present invention.

Cellular Receptor PTK Assays

The following cellular assay was used to determine the level of activity and effect of the different compounds of the present invention on KDR/VEGFR2. Similar receptor PTK assays employing a specific ligand stimulus can be designed along the same lines for other tyrosine kinases using techniques well known in the art.

KDR Cellular Assay

The ability of compounds to inhibit KDR receptor phosphorylation in cells was measured by ELISA following the protocol outlined below.

Day 1 Protocol

KDR transfected 3T3 (embryonic mouse) cells added to 96-well tissue culture plates at 20,000 cells/well.

Plates were covered and placed in a 37° C. humidified incubator with 5% $CO_2$ overnight, to allow cells to adhere.

Coating solution was prepared: 500 µl/vial PBS was added to 2 vials of anti-KDR antibody, then 1 ml solubilized anti-KDR antibody into 29.0 ml bicarbonate buffer.

Coating solution was added to all wells at 150 µl/well (final amount anti-KDR=1 µg/well) and placed at 4° C. overnight Day 2 Protocol Blocking solution (2.1 g dry milk+42 ml PBS=5% milk in PBS) was placed on a stir plate for 30 min.

Assay plates were washed twice with PBST, and 200 µl/well blocking solution was added to all wells. Assay plates were covered with plate sealers and placed in a 37° C. microplate chamber until just before cell lysate transfer.

Compound stocks were thawed or prepared in DMSO as 5 mM stocks.

Dilution medium (DM, 1% DMSO in DMEM) and compounds were diluted by half-log increments for concentration response analysis.

Conditioned media was dumped from the tissue culture plates, and plates were blotted dry.

Standard solution in DM, compound dilutions in DM, or DM (for high control, negative control, and reference wells) were added to the tissue culture plates, 25 µl/well. Each pair of tissue culture plates was prepared with the same compounds, solutions, and layout; and will be combined later, Tissue culture plates were covered and placed in the 37° C. microplate chamber for 20 min.

VEGF solution was prepared: 110 µl VEGF stock+10.89 ml DM=100 ng/ml VEGF

VEGF solution or DM (for reference wells) was added to the tissue culture plates, 25 µl/well.

Tissue culture plates were covered and placed in the 37° C. microplate chamber for 10 min.

RIPA buffer was prepared (240 µl NaVO3 stock+240 µl PIC stock+24 µl NaF stock+23.496 ml RIPA base) and added to the tissue culture plates, 50 µl/well.

Tissue culture plates were covered and placed on a Labline plate shaker for 10 min (speed about 5).

Assay plates were washed twice with PBST.

Cell lysates from matching wells of each pair of tissue culture plates were combined to=200 µl/well, and were pipetted up and down to mix.

Cell lysates were transferred to the assay plates using the same layouts, 170 µl/well.

Assay plates were covered with plate sealers and placed on a Labline plate shaker for 2 hr (speed about 5).

Assay plates were washed 5 times with PBST.

Biotin antibody solution was prepared (16 µl biotin antibody stock+32 ml PBST=2000× dilution) and added to the assay plates, 150 µl/well.

Assay plates were covered with plate sealers and placed on a Labline plate shaker for 90 min Assay plates were washed 5 times with PBST.

Streptavidin-HRP solution was prepared (16 µl streptavidin-HRP stock+32 ml PBST=2000× dilution) and added to the assay plates, 150 µl/well.

Assay plates were covered with plate sealers and placed on a Labline plate shaker for 60 min Assay plates were washed 5 times with PBST.

Substrate was added to the assay plates, 100 µl/well.

As assay plates developed, the plates were each monitored on a Molecular Devices Spectramax set to 650 nm, until the signal in the high control wells was around 0.6 OD and the signal in the negative control wells was around 0.1-0.15 OD.

Stop solution was added to the assay plates, 100 µl/well.

The plates were read on a Molecular Devices Spectramax set to 450 nm.

Data was calculated by Assay Explorer, using same-plate high control wells as 0% and reference standard wells as 100% inhibition of KDR phosphorylation. $IC_{50}$ values were calculated by non-linear regression analysis of the concentration response data.

Reagents & Materials 96-well tissue culture plate: flat bottom tissue culture-treated, Costar 3599
PBS: 1× phosphate-buffered saline, pH 7.4, without calcium chloride, without magnesium chloride; Invitrogen/Gibco 10010 lot 1187052+1201198
Anti-KDR antibody: anti-human VEGF R2 (KDR) antibody, R&D Systems AF357 lot CUE02405A, 5 mg per vial at 2.630 mg/ml; divided into 38 µl aliquots; stored at −30° C.
Bicarbonate buffer: 1 packet BupH carbonate-bicarbonate buffer pack (Pierce 28382 lot DH58189B)+500 ml nH2O, stored at room temperature
96-well assay plate: EIA/RIA Easywash plate, high binding; Costar 3369
Dry milk: Biorad 170-6404 lot 175026B
PBST: 1 ml tween+1L PBS=1% tween in PBS, stored at room-temperature
Tween: Tween 20, Sigma P-1379 lot 033K0711
DMEM 11965: Dulbecco's modified Eagle medium, high glucose, with L-glutamine, with pyroxidine hydrochloride, without sodium pyruvate; Invitrogen/Gibco 11965 lot 1212380
VEGF stock: 1 ml PBS/BSA (PBS+0.1% BSA, prepared by Keith Glaser and stored at room temperature, catalog and lot numbers unknown) added to 1 vial VEGF (recombinant human VEGF, R&D Systems 293-VE lot II16311, 10 µg per vial)=10 µg/ml; divided into 55 µl aliquots; stored at −80° C.
NaVO3 stock: 12.19 mg/ml sodium metavanadate (Sigma S-6383 lot 092K0853, FW 121.9) in nH2O=100 mM, heated at 37° C. to solubilize, then divided into 120 µl aliquots; stored at −20° C.; final concentartion 1 mM in RIPA buffer
PIC stock: protease inhibitor cocktail (Sigma P-8340 lot 044K4106); divided into 120 µl aliquots; stored at −20° C.; final dilution 100× in RIPA buffer
NaF stock: 41.99 mg/ml sodium fluoride (Sigma S-7920 lot 070K0120, FW 41.99) in nH2O=1 M, divided into 12 µl aliquots; stored at −20° C.; final concentration 1 mM in RIPA buffer
RIPA base: prepared in nH2O to 500 ml final volume with components below, pH'd to 7.4; stored at 4° C.
   3.94 g Trizma hydrochloride (Sigma T-3253 lot 108H5406, FW 157.6)=50 mM
   5.0 ml Igepal CA-630 (Sigma I-3021 lot 122K0040)=1%
   1.25 g deoxycholic acid, sodium salt (Sigma D-6750 lot 44F-0504, FW 414.5)=0.25%
   4.383 g NaCl (Fisher S271-3 lot 005493, FW 58.44)=150 mM
   226.1 mg EDTA (Sigma E-5391 lot 33H0478, FW 452.2)=1 mM
Biotin antibody stock: anti-phosphotyrosine, biotin-conjugate, mouse monoclonal IgG2bκ, clone 4G10; Upstate Biotechnology 16-103 lot 23957
Streptavidin-HRP stock: streptavidin, horseradish peroxidase conjugate; Upstate Biotechnology 18-152 lot 26275, bottle opened Jul. 1, 2004
Substrate: Enhanced K-blue substrate (TMB), Neogen 308177 lot 040405
Stop solution: 14.5 ml phosphoric acid (Sigma P-5811 lot 051K3451, FW 98.00, 17.245 M)+235.5 ml nH2O=1 M; stored at room temperature In Vivo Uterine Edema Model This assay measures the capacity of compounds to inhibit the acute increase in uterine weight in mice which occurs in the first few hours following estrogen stimulation. This early onset of uterine weight increase is known to be due to edema caused by increased permeability of uterine vasculature. Cullinan-Bove and Koss (Endocrinology (1993), 133:829-837) demonstrated a close temporal relationship of estrogen-stimulated uterine edema with increased expression of VEGF mRNA in the uterus. These results have been confirmed by the use of neutralizing monoclonal antibody to VEGF which significantly reduced the acute increase in uterine weight following estrogen stimulation (WO 97/42187). Hence, this system can serve as a model for in vivo inhibition of VEGF signalling and the associated hyperpermeability and edema.

Materials: All hormones can be purchased from Sigma (St. Louis, Mo.) or Cal Biochem (La Jolla, Calif.) as lyophilized powders and prepared according to supplier instructions.

Vehicle components (DMSO, Cremaphor EL) can be purchased from Sigma (St. Louis, Mo.).

Mice (Balb/c, 8-12 weeks old) can be purchased from Taconic (Germantown, N.Y.) and housed in a pathogen-free animal facility in accordance with institutional Animal Care and Use Committee Guidelines.

Method:

Day 1: Balb/c mice are given an intraperitoneal (i.p.) injection of 12.5 units of pregnant mare's serum gonadotropin (PMSG).

Day 3: Mice receive 15 units of human chorionic gonadotropin (hCG) i.p.

Day 4: Mice are randomized and divided into groups of 5-10. Test compounds are administered by i.p., i.v. or p.o. routes depending on solubility and vehicle at doses ranging from 1-100 mg/kg. Vehicle control group receive vehicle only and two groups are left untreated.

Thirty minutes later, experimental, vehicle and 1 of the untreated groups are given an i.p. injection of 17-estradiol (500 mg/kg). After 2-3 hours, the animals are sacrificed by $CO_2$ inhalation. Following a midline incision, each uterus was isolated and removed by cutting just below the cervix and at the junctions of the uterus and oviducts. Fat and connective tissue were removed with care not to disturb the integrity of the uterus prior to weighing (wet weight). Uteri are blotted to remove fluid by pressing between two sheets of filter paper with a one liter glass bottle filled with water. Uteri are weighed following blotting (blotted weight). The difference between wet and blotted weights is taken as the fluid content of the uterus. Mean fluid content of treated groups is compared to untreated or vehicle treated groups. Significance is determined by Student's test Non-stimulated control group is used to monitor estradiol response.

The compounds of the present invention may be used in the treatment of protein kinase-mediated conditions, such as benign and neoplastic proliferative diseases and disorders of the immune system. Such diseases include autoimmune diseases, such as rheumatoid arthritis, thyroiditis, type 1 diabetes, multiple sclerosis, sarcoidosis, inflammatory bowel disease, Crohn's disease, myasthenia gravis and systemic lupus erythematosus; psoriasis, organ transplant rejection (e.g., kidney rejection, graft versus host disease), benign and neoplastic proliferative diseases, human cancers such as lung, breast, stomach, bladder, colon, pancreatic, ovarian, prostate and rectal cancer and hematopoietic malignancies (leukemia and lymphoma), glioblastoma, infantile hemangioma, and diseases involving inappropriate vascularization (for example diabetic retinopathy, retinopathy of prematurity, choroidal neovascularization due to age-related macular degeneration, and infantile hemangiomas in human beings). Such inhibitors may be useful in the treatment of disorders involving VEGF mediated edema, ascites, effusions, and exudates, including for example macular edema, cerebral edema, acute lung injury and adult respiratory distress syndrome (ARDS). In addition, the compounds of the invention may be useful in the treatment of pulmonary hypertension, particularly in patients with thromboembolic disease (J. Thorac. Cardiovasc. Surg. 2001, 122 (1), 65-73).

This invention is intended to encompass compounds having formula (I) when prepared by synthetic processes or by metabolic processes. Preparation of the compounds of the invention by metabolic processes include those occurring in the human or animal body (in vivo) or processes occurring in vitro.

Synthetic Methods

Abbreviations which have been used in the descriptions of the scheme and the examples that follow are: nBu for n-butyl; dppf for diphenylphosphinoferrocene; DMF for N,N-dimethylformamide; DME for 1,2-dimethoxyethane; HPLC for high pressure liquid chromatography; NMP for N-methylpyrrolidinone; DMSO for dimethylsulfoxide; min for minutes; and THF for tetrahydrofuran.

The compounds and processes of the present invention will be better understood in connection with the following synthetic schemes which illustrate the methods by which the compounds of the invention may be prepared. Starting materials can be obtained from commercial sources or prepared by well-established literature methods known to those of ordinary skill in the art.

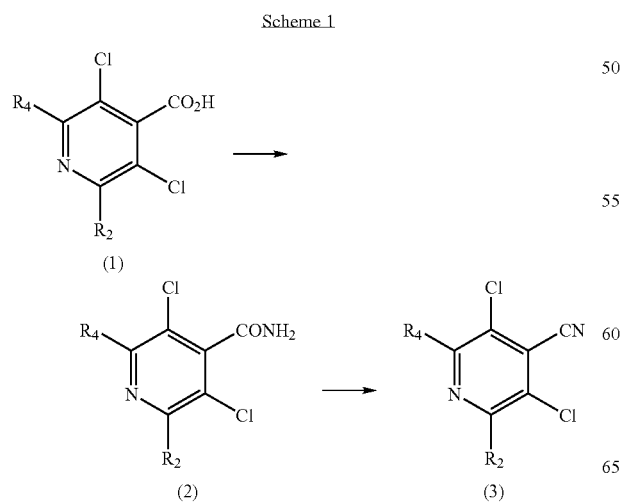

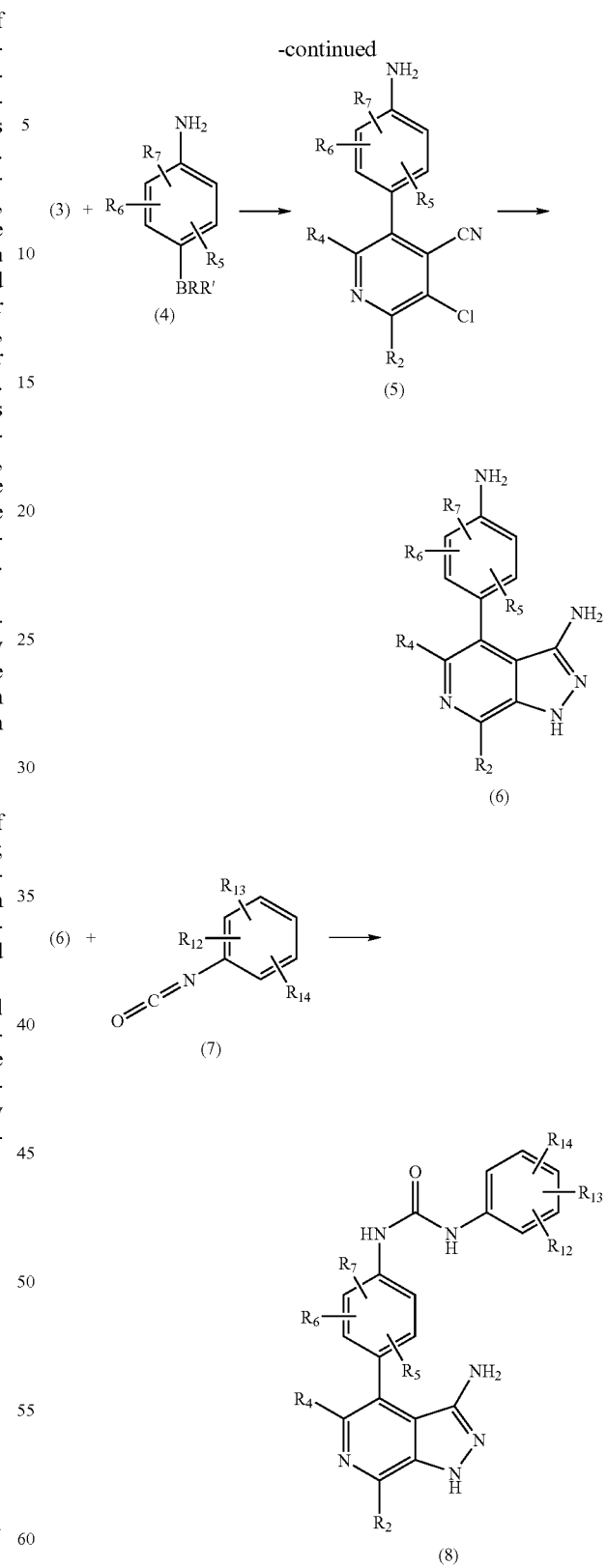

Compounds of formula (8), wherein $R_2$, $R_4$, $R_5$, $R_6$, $R_7$, $R_{12}$, $R_{13}$, and $R_{14}$ are as defined in formula (I), can be prepared as described in Scheme 1. Pyridine acids of formula (1), purchased commercially or prepared using methodology well known to those of skill in the art, can be treated with an activating agent such as oxalyl chloride and ammonia to provide amides of formula (2). Amides of formula (2) can be treated with a dehydrating agent such as phosphorous oxychloride to provide cyanides of formula (3). Cyanides of general formula (3) can be treated with boronic acids or boronates of formula (4), (R and R' can be alkoxy or hydroxy), a palladium catalyst, and a base to provide compounds of formula (5). Compounds of formula (5) can be treated with hydrazine to provide compounds of formula (6). Compounds of formula (6) can be treated with isocyanates of formula (7) to provide ureas of formula (8).

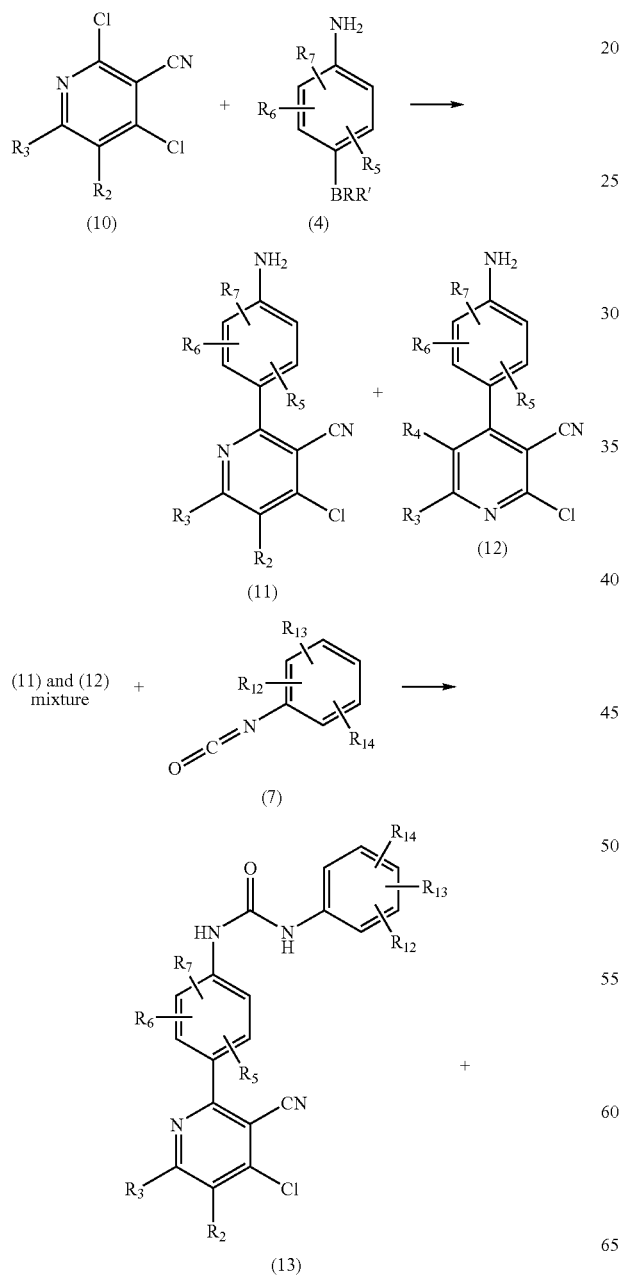

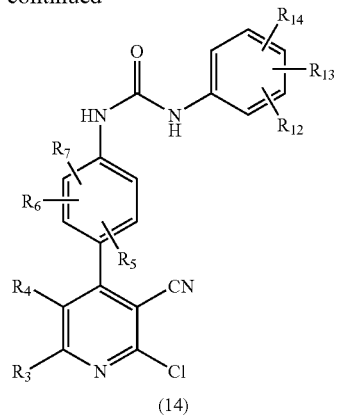

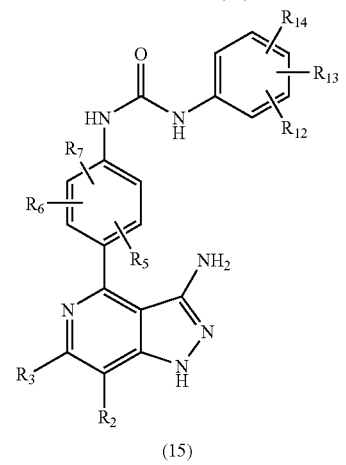

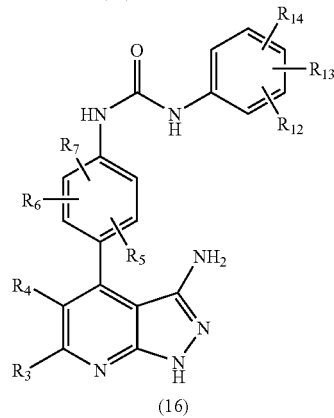

Compounds of formula (15) and compounds of formula (16), wherein $R_2$, $R_3$, $R_4$, $R_5$, $R_6$, $R_7$, $R_{12}$, $R_{13}$, and $R_{14}$ are as defined in formula (I), can be prepared as described in Scheme 2. Compounds of formula (10), purchased or prepared using methodology well known to those of skill in the art, can be treated with boronic acids or boronates of formula (4) (R and R' can be alkoxy or hydroxy), a palladium catalyst, and a base to provide compounds of formula (11) and compounds of formula (12). The mixture of compounds of formula (11) and formula (12) can be separated or treated with isocyanates of formula (7) to provide a mixture of ureas of formula (13) and formula (14). The mixture of ureas can be separated or treated with hydrazine to provide compounds of formula (15) and formula (16) which can be separated using techniques well known to those of skill in the art.

Compounds of the present invention were named by ACD/ChemSketch version 5.0 (developed by Advanced Chemistry Development, Inc., Toronto, ON, Canada) or were given names which appeared to be consistent with ACD nomenclature.

EXAMPLE 1

N-[4-(3-amino-1H-pyrazolo[3,4-c]pyridin-4-yl)phenyl]-N'-(2-fluoro-5-methylphenyl)urea

EXAMPLE 1A 3,5-Dichloroisonicotinamide

A solution of 3,5-dichloro-isonicotinic acid (9.54 g, 49.6 mmol, commercially available form TCI) in benzene (100 mL) was treated with oxalyl chloride (8.7 mL), a catalytic amount of DMF (5 drops), stirred overnight at room temperature, and concentrated under reduced pressure. The residue was dissolved in diglyme (10 mL) and added dropwise to 35% $NH_2OH$ in water (150 mL). The mixture was filtered to provide 8.2 g of the title compound as a white powder. MS ((DCI (+)) m/e 190.9 $(M+H)^+$.

EXAMPLE 1B 3,5-Dichloro-isonicotinonitrile

The product from Example 1A (2.1 g, 11 mmol) in $POCl_3$ (25 mL) was stirred at reflux overnight, allowed to cool to room temperature, poured onto ice, and extracted with ethyl acetate. The organic extract was dried ($Na_2SO_4$), filtered, and the filtrate was concentrated under reduced pressure to give 1.2 g of the title compound. $^1$H NMR (300 MHz, DMSO-$D_6$) δ ppm 8.96 (s, 2H).

EXAMPLE 1C 3-(4-Amino-phenyl)-5-chloro-isonicotinonitrile

The product from Example 1B (3 g, 17.3 mmol), 4-(4,4,5,5-tetramethyl-[1,3,2]dioxaborolan-2-yl)-phenylamine (4.18 g, 19 mmol), $PdCl_2$dppf.$CH_2Cl_2$ (300 mg), and $Na_2CO_3$ (4.5 g) were combined in DMF (25 mL) and water (10 mL). The mixture was degassed with nitrogen and heated to 85° C. overnight The mixture was allowed to cool to room temperature and partitioned between water and ethyl acetate. The organic layer was dried ($Na_2SO_4$), filtered, and the filtrate was concentrated under reduced pressure. The residue was purified via silica gel chromatography eluting with hexanes:ethyl acetate (1:1) to provide 1.4 g of the title compound. $^1$H NMR (300 MHz, DMSO-$D_6$) δ ppm 5.67 (s, 2H) 6.70 (d, J=8.48 Hz, 2H) 7.40 (d, J=8.82 Hz, 2H) 8.76 (s, 1H) 8.79 (s, 1H).

EXAMPLE 1D 4-(4-Amino-phenyl)-1H-pyrazolo[3,4-c]pyridin-3-ylamine

The product from Example 1C (1.4 g) in hydrazine hydrate (10 mL) was heated at 110° C. for 3 hours, cooled to room temperature, and partitioned between water and ethyl acetate. The organic layer was dried ($Na_2SO_4$), filtered, and the filtrate was concentrated under reduced pressure. The residue was purified via silica gel chromatography eluting with 8% methanol in $CH_2Cl_2$ to provide 0.5 g of the title compound as a yellow solid. MS (ESI(+)) m/e 225 $(M+H)^+$.

EXAMPLE 1E

N-[4-(3-amino-1H-pyrazolo[3,4-c]pyridin-4-yl)phenyl]-N'-(2-fluoro-5-methylphenyl)urea The product from Example 1D (50 mg, 0.22 mmol) in DMF (1 mL) was treated with 1-fluoro-2-isocyanato-4-methyl-benzene (0.03 mL, 0.22 mmol) and stirred for 16 hours. The crude product was directly purified via preparative HPLC on an Agilent Zorbax Stablebond C-18 (7 micron particle size) preparative column using a solvent gradient of 30% to 100% acetonitrile in 0.1% aqueous TFA at a flow rate of 15 mL/minute. The product was further purified via silica gel chromatography eluting with 5% methanol/$CH_2Cl_2$ to provide 4 mg of the title compound. MS (ESI(+)) m/e 377 $(M+H)^+$; $^1$H NMR (300 MHz, DMSO-$D_6$) δ ppm 2.28 (s, 3H) 4.61 (s, 2H) 6.77-6.85 (m, 1H) 7.12 (dd, J=11.53, 8.14 Hz, 1H) 7.49 (d, J=8.81 Hz, 2H) 7.63 (d, J=8.48 Hz 2 H) 7.94 (s, 1H) 8.01 (dd, J=8.31, 1.86 Hz, 1H) 8.55 (d, J=2.71 Hz, 1H) 8.73 (s, 1H) 9.24 (s, 1H) 12.26 (s, 1H).

EXAMPLE 2

N-[4-(3-amino-1H-pyrazolo[3,4-c]pyridin-4-yl)phenyl]-N'-(3-methylphenyl)urea

The title compound was prepared using the procedure described in Example 1E using 1-isocyanato-3-methyl-benzene instead of 1-fluoro-2-isocyanato-4-methyl-benzene. MS (APCI(+)) m/z 359 $(M+H)^+$; $^1$H NMR (300 MHz, DMSO-$D_6$) δ ppm 2.29 (s, 3H) 4.61 (s, 2H) 6.80 (d, J=7.12 Hz, 1H) 7.17 (t, J=7.80 Hz, 1H) 7.26 (d, J=7.80 Hz, 1H) 7.32 (s, 1H) 7.47 (d, J=8.81 Hz, 2H) 7.63 (d, J=8.81 Hz, 2H) 7.93 (s, 1H) 8.66 (s, 1H) 8.73 (s, 1H) 8.84 (s, 1H) 12.26 (s, 1H).

EXAMPLE 3

N-[4-(3-amino-1H-pyrazolo[3,4-c]pydridin-4yl)phenyl]-N'-(3-chlorophenyl)urea

The title compound was prepared using the procedure described in Example 1E using 1-chloro-3-isocyanato-benzene instead of 1-fluoro-2-isocyanato-4-methyl-benzene. MS (ESI(+)) m/e 379 $(M+H)^+$; $^1$H NMR (300 MHz, DMSO-$D_6$) δ ppm 7.02-7.06 (m, 1H) 7.29-7.33 (m, 2H) 7.55 (d, J=8.82 Hz, 2H) 7.69 (d, J=8.82 Hz, 2H) 7.75 (s, 1H) 8.10 (s, 1H) 9.07 (s, 1H) 9.12 (s, 2H).

EXAMPLE 4

N-[4-(3-amino-1H-pyrazolo[3,4-c]pyridin-4-yl)phenyl]-N'-[2-fluoro-5-(trifluoromethyl)phenyl]urea The title compound was prepared using the procedure described in Example 1E using 1-fluoro-2-isocyanato-4-trifluoromethyl-benzene instead of 1-fluoro-2-isocyanato-4-methylbenzene. MS (ESI(+))m/e 431 $(M+H)^+$; $^1$H NMR (300 MHz, DMSO-$D_6$) δ ppm 7.39-7.45 (m, 1 H) 7.51 (d, J=10.85

Hz, 1H) 7.56 (d, J=8.48 Hz, 2H) 7.70 (m, 2H) 8.08 (s, 1H) 8.64 (dd, J=7.29, 2.20 Hz, 1H) 9.00 (d, J=2.71 Hz, 1H) 9.07 (s, 1H) 9.44 (s, 1H)

EXAMPLE 5

N-[4-(3-amino-1H-pyrazolo[3,4-c]pyridin-4-yl)phenyl]-N'-(4-fluoro-3-methylphenyl)urea The title compound was prepared using the procedure described in Example 1E using 1-fluoro-4-isocyanato-2-methyl-benzene instead of 1-fluoro-2-isocyanato-4-methyl-benzene. MS (ESI(+)) m/e 377 (M+H)$^+$; $^1$H NMR (300 MHz, DMSO-D$_6$) δ ppm 2.22 (d, J=1.70 Hz, 3H) 4.61 (s, 2H) 7.06 (t, J=9.15 Hz, 1H) 7.24-7.32 (m, 1H) 7.38 (dd, J=6.78, 2.37 Hz, 1H) 7.47 (d, J=8.48 Hz, 2H) 7.62 (d, J=8.48 Hz, 2H) 7.93 (s, 1H) 8.68 (s, 1H) 8.73 (s, 1H) 8.85 (s, 1H) 12.26 (s, 1H).

EXAMPLE 6

N-[4-(3-amino-1-methyl-1H-pyrazolo[3,4-c]pyridin-4-yl)phenyl]-N'-(2-fluoro-5-methylphenyl)urea

EXAMPLE 6A 4-(4-Amino-phenyl)-1-methyl-1H-pyrazolo[3,4-c]pyridin-3-ylamine

The product from Example 1C (150 mg, 0.65 mmol) and methylhydrazine (0.35 mL) in n-butanol (2 mL) was heated in a sealed vial at 190° C. for 30 minutes with stirring in a Smith Synthesizer microwave oven (at 300W). The reaction mixture was allowed to cool to room temperature and partitioned between water and ethyl acetate. The organic extract was dried (Na$_2$SO$_4$), filtered, and the filtrate was concentrated to provide 0.08 g of the title compound. MS (ESI(+)) m/e 240 (M+H)$^+$.

EXAMPLE 6B

N-[4-(3-amino-1-methyl-1H-pyrazolo[3,4-c]pyridin-4-yl)phenyl]-N'-(2-fluoro-5-methylphenyl)urea The title compound was prepared using the procedure described in Example 1E using the product from Example 6A instead of the product from Example 1D. MS (ESI(+)Q1MS m/z 391 (M+H)$^+$; $^1$H NMR (300 MHz, DMSO-D$_6$) δ ppm 2.28 (s, 3H) 4.02 (s, 3H) 6.80-6.85 (m, 1H) 7.12 (dd, J=11.36, 8.31 Hz, 1H) 7.53 (d, J=8.81 Hz, 2H) 7.67 (d, J=8.81 Hz, 2H) 7.99 (dd, J=8.31, 2.20 Hz, 1H) 8.10 (s, 1H) 8.57 (d, J=2.37 Hz, 1H) 9.20 (s, 1H) 9.31 (s, 1H).

EXAMPLE 7

N-[4-(3-amino-1-methyl-1H-pyrazolo[3,4-c]pyridin-4-yl)phenyl]-N'-(3-methylphenyl)urea The title compound was prepared using the procedure described in Example 1E using the product from Example 6A and 1-isocyanato-3-methyl-benzene instead of the product from Example 1D and 1-fluoro-2-isocyanato-4-methyl-benzene. MS (ESI(+)) m/e 373 (M+H)$^+$; $^1$H NMR (300 MHz, DMSO-D$_6$) δ ppm 2.29 (s, 3H) 4.02 (s, 3H) 6.81 (d, J=7.12 Hz, 1H) 7.17 (t, J=7.80 Hz, 1H) 7.26 (d, J=8.14 Hz, 1H) 7.32 (s, 1H) 7.52 (d, J=8.82 Hz, 2H) 7.68 (d, J=8.82 Hz, 2H) 8.10 (s, 1H) 8.71 (s, 1H) 8.95 (s, 1H) 9.20 (s, 1H).

EXAMPLE 8

N-[4-(3-amino-1-methyl-1H-pyrazolo[3,4-c]pyridin-4-yl)phenyl]-N'-(3-chlorophenyl)urea The title compound was prepared using the procedure described in Example 1E using the product from Example 6A and 1-chloro-3-isocyanato-benzene instead of the product from Example 1D and 1-fluoro-2-isocyanato-4-methyl-benzene. MS (ESI(+)) m/e 393 (M+H)$^+$; $^1$H NMR (300 MHz, DMSO-D$_6$) δ ppm 3.92 (s, 3H) 4.67 (s, 2H) 7.01-7.06 (m, 1H) 7.29-7.34 (m, 2H) 7.48 (d, J=8.48 Hz, 2H) 7.63 (d, J=8.48 Hz, 2H) 7.73 (s, 1H) 7.95 (s, 1H) 8.87 (s, 1 H) 8.97 (br.s, 2H).

EXAMPLE 9

N-[4-(3-amino-1-methyl-1H-pyrazolo[3,4-c]pyridin-4-yl)phenyl]-N'-(3-fluorophenyl)urea The title compound was prepared using the procedure described in Example 1E using the product from Example 6A and 1-fluoro-3-isocyanato-benzene instead of the product from Example 1D and 1-fluoro-2-isocyanato-4-methyl-benzene. MS (ESI(+)) m/e 377 (M+H)$^+$; $^1$H NMR (300 MHz, DMSO-D$_6$) δ ppm 3.92 (s, 3H) 4.67 (s, 2H) 6.80 (td, J=8.31, 2.37 Hz, 1H) 7.15 (dd, J=8.31, 1.19 Hz, 1H) 7.32 (q, 1H) 7.48 (d, J=8.48 Hz, 2H) 7.53 (t, J=2.37 Hz, 1H) 7.63 (d, J=8.48 Hz, 2H) 7.95 (s, 1H) 8.87 (s, 1H) 8.95 (s, 1H) 8.99 (s, 1H)

EXAMPLE 10

N-[4-(3-amino-1-methyl-1H-pyrazolo[3,4-c]pyridin-4-yl)phenyl]-N'-(3-chloro-4-fluorophenyl)urea The title compound was prepared using the procedure described in Example 1E using the product from Example 6A and 2-chloro-1-fluoro-4-isocyanato-benzene instead of the product from Example 1D and 1-fluoro-2-isocyanato-4-methyl-benzene. MS (ESI(+)) m/e 411 (M+H)$^+$; $^1$H NMR (300 MHz, DMSO-D$_6$) δ ppm 3.92 (s, 3H) 4.61-4.72 (m, 2H) 7.32-7.37 (m, 2H) 7.47 (d, J=8.82 Hz, 2H) 7.63 (d, J=8.82 Hz, 2H) 7.79-7.84 (m, 1H) 7.94 (s, 1H) 8.87 (s, 1H) 8.95 (s, 1H) 8.96 (s, 1H).

EXAMPLE 11

N-[4-(3-amino-1-methyl-1H-pyrazolo[3,4-c]pyridin-4-yl)phenyl]-N'-(4-fluoro-3-methylphenyl)urea The title compound was prepared using the procedure described in Example 1E using the product from Example 6A and 1-fluoro-4-isocyanato-4-methyl-benzene instead of the product from Example 1D and 1-fluoro-2-isocyanato-4-methyl-benzene. MS (ESI(+)) m/e 391 (M+H)$^+$; $^1$H NMR (300 MHz, DMSO-D$_6$) δ ppm 2.22 (d, J=1.70 Hz, 3H) 4.02 (s, 3H) 7.06 (t, J=9.15 Hz, 1H) 7.24-7.33 (m, 1H) 7.35-7.43 (m, 1H) 7.52 (d, J=8.81 Hz, 2H) 7.67 (d, J=8.81 Hz, 2H) 8.10 (s, 1H) 8.77 (s, 1H) 8.99 (s, 1H) 9.21 (s, 1H).

EXAMPLE 12

N-[4-(3-amino-1-methyl-1H-pyrazolo[3,4-c]pyridin-4-yl)phenyl]-N'-[3-(trifluoromethyl)phenyl]urea The title compound was prepared using the procedure described in Example 1E using the product from Example 6A and 1-isocyanato-3-trifluoromethyl-benzene instead of the product from Example 1D and 1-fluoro-2-isocyanato-4-methyl-benzene. MS (ESI(+)) m/e 427 (M+H)+; $^1$H NMR (500 MHz, DMSO-D$_6$) δ ppm 3.92 (s, 3H) 4.66 (s, 2H) 7.33 (d, J=7.49 Hz, 1H) 7.48 (d, J=8.73 Hz, 2H) 7.53 (t, J=7.95 Hz, 1H) 7.61 (d, J=9.05 Hz, 1H) 7.65 (d, J=8.73 Hz, 2H) 7.95 (s, 1H) 8.04 (s, 1H) 8.87 (s, 1H) 8.98 (s, 1H) 9.10 (s, 1H).

EXAMPLE 13

N-[4-(3-amino-1-methyl-1H-pyrazolo[3,4-c]pyridin-4-yl)phenyl]-N'-[2-fluoro-5-(trifluoromethyl)phenyl]urea The title compound was prepared using the procedure described in Example 1E using the product from Example 6A and 1-fluoro-2-isocyanato-4-trifluoromethyl-benzene instead of the product from Example 1D and 1-fluoro-2-isocyanato-4-methyl-benzene. MS (ESI(+)) m/e 445 (M+H)+; $^1$H NMR (500 MHz, DMSO-D$_6$) δ ppm 3.92 (s, 3H) 4.66 (s, 2H) 7.36-7.45 (m, 1H) 7.46-7.55 (m, 1H) 7.50 (d, J=8.73 Hz, 2H) 7.65 (d, J=8.42 Hz, 2H) 7.95 (s, 1H) 8.64 (dd, J=7.33, 2.03 Hz, 1H) 8.87 (s, 1H) 8.95 (d, J=2.81 Hz, 1H) 9.35 (s, 1H).

EXAMPLE 14

N-[4-(3-amino-1H-pyrazolo[4,3-c]pyridin-4-yl)phenyl]-N'-(2-fluoro-5-methylphenyl)urea

EXAMPLE 14A 2,4-Dichloro-nicotinic acid

Lithium diisopropylamide (2M in heptane/THF/benzene, 16.7 mL) was treated dropwise with 2,4-dichloropyridine (5 g, 33.8 mmol) at −78° C. in THF (25 mL). The mixture was stirred at −78° C. for 2 hours, treated with excess dry ice, allowed to warm up to room temperature, and partitioned between diethyl ether and an equal volume of 10% aqueous KOH. The basic extract was neutralized with 10% HCl and extracted with diethyl ether. The ethereal extract was dried (Na$_2$SO$_4$), filtered, and the filtrate wasconcentrated under reduced pressure to provide 9.5 g (70% yield) of the title compound. $^1$H NMR (300 MHz, DMSO-D$_6$) δ ppm 3.32 (s, 1H), 7.74 (d, J=5.42 Hz,1H), 8.47 (d, J=5.42 Hz,1H).

EXAMPLE 14B 2,4-Dichloro-nicotinonitrile

The title compound was prepared using the procedures described in Example 1A and Example 1B using the product from Example 14A instead of 3,5-dichloroisonicotinic acid. $^1$H NMR (300 MHz, DMSO-D$_6$) δ ppm 7.93 (d, J=5.76 Hz,1H), 8.67 (d, J=5.76 Hz,1H).

EXAMPLE 14C 4-(4-aminophenyl)-2-chloronicotinonitrile and 2-(4-aminophenyl)-4-chloronicotinonitrile The title compounds were prepared as an inseperable mixture using the procedure described in Example 1C using the product from Example 14B instead of the product from Example 1B. MS (ESI(+)) m/e 229.9 (M+H)+.

EXAMPLE 14D

N-[4-(2-chloro-3-cyanopyridin-4-yl)phenyl]-N'-(2-fluoro-5-methylphenyl)urea and

N-[4-(4-chloro-3-cyanopyridin-2-yl)phenyl]-N'-(2-fluoro-5-methylphenyl)urea

The mixture from Example14C (52 mg, 0.23 mmol) in CH$_2$Cl$_2$ (2 mL) was teated dropwise with 1-fluoro-2-isocyanato-4-methyl-benzene (0.032 mL) at 0° C. After stirring at room temperature overnight, the mixture was filtered and the filter cake was dried to provide 58 mg of a 2 to 1 mixture of the title compounds. MS (ESI(+)) m/e 376.9 (M+H)+.

EXAMPLE 14E

N-[4-(3-amino-1H-pyrazolo[4,3-c]pyridin-4-yl)phenyl]-N'-(2-fluoro-5-methylphenyl)urea The mixture of Example 14D (250 mg) in nBuOH (5 mL) was treated with hydrazine monohydrate (2.5 mL), heated to 110° C. for 4 h, allowed to cool to room temperature and concentrated. The residue was purified via HPLC on an Agilent Zorbax Stablebond C-18 (7 micron particle size) preparative column using a solvent gradient of 20% to 100% acetonitrile in 0.1% aq. TFA at a flow rate of 15 ml/min over 50 min, to give 40 mg of the title compound. MS (ESI(+))m/e 377 (M+H)+; $^1$H NMR (300 MHz, DMSO-D$_6$) δ ppm 2.29 (s, 3H) 6.79-6.90 (m, 1 H) 7.14 (dd, J=11.53, 8.48 Hz, 1H) 7.62-7.69 (m, 1H) 7.72-7.84 (m, 4H) 7.98 (dd, J=7.63, 2.20 Hz, 1H) 8.22 (s, 1H) 8.67 (d, J=2.71 Hz, 1H) 9.53 (s, 1H).

EXAMPLE 15

N-[4-(3-amino-1H-pyrazolo[3,4-b]pyridin-4-yl)phenyl]-N'-(2-fluoro-5-methylphenyl)urea The mixture of Example 14D (250 mg) in nBuOH (5 mL) was treated with hydrazine monohydrate (2.5 mL), heated to 110° C. for 4 h, allowed to cool to room temperature and concentrated. The residue was purified via HPLC on an Agilent Zorbax Stablebond C-18 (7 micron particle size) preparative column using a solvent gradient of 20% to 100% acetonitrile in 0.1% aq. TFA at a flow rate of 15 ml/min over 50 min, to give 25 mg of the title compound. MS (ESI(+)) m/e 377 (M+H)+; $^1$H NMR (300 MHz, DMSO-D$_6$) δ ppm 2.28 (s, 3H) 6.78-6.86 (m, 1 H) 6.93 (d, J=4.75 Hz, 1H) 7.12 (dd, J=11.36, 8.31 Hz, 1H) 7.56 (d, J=8.82 Hz, 2H) 7.66 (d, J=8.82 Hz, 2H) 8.00 (dd, J=7.63, 2.20 Hz, 1H) 8.39 (d, J=4.75 Hz, 1H) 8.56 (d, J=2.71 Hz, 1 H) 9.30 (s, 1H).

EXAMPLE 16

N-[4-(3-amino-1H-pyrazolo[4,3-c]pyridin-4-yl)phenyl]-N'-[2-fluoro-5-(trifluoromethyl)phenyl]urea

EXAMPLE 16A

N-[4-(2-chloro-3-cyanopyridin-4-yl)phenyl]-N'-[2-fluoro-5-trifluoromethyl)phenyl]urea and N-[4-(4-chloro-3-cyanopyridin-2-yl)phenyl]-N'-[2-fluoro-5-(trifluoromethyl)phenyl]urea The title compounds were prepared using the procedure described in Example 14D except using 1-fluoro-2-isocyanato-4-trifluoromethyl-benzene instead of 1-fluoro-2-isocyanato-4-methyl-benzene.

EXAMPLE 16B

N-[4-(3-amino-1H-pyrazolo[4,3-c]pyridin-4-yl)phenyl]-N'-[2-fluoro-5-(trifluoromethyl)phenyl]urea The title compound was prepared using the procedure described in Example 14E except using the mixture from Example 16A instead of the mixture from Example 14D. MS (ESI(+)) m/e 431 (M+H)$^+$; $^1$H NMR (300 MHz, DMSO-D$_6$) δ ppm 7.39-7.50 (m, 1H) 7.54 (t, 1H) 7.67 (d, J=6.78 Hz, 1H) 7.73-7.87 (m, 4H) 8.21 (d, J=7.12 Hz, 1H) 8.62 (dd, J=7.29, 2.20 Hz, 1H) 9.10 (d, J=2.71 Hz, 1H) 9.67 (s, 1H).

EXAMPLE 17

N-[4-(3-amino-1H-pyrazolo[3,4-b]pyridin-4-yl)phenyl]-N'-[2-fluoro-5-(trifluoromethyl)phenyl]urea The title compound was prepared using the procedure described in Example 14E except using the mixture from Example 16A instead of the mixture from Example 14D. MS (ESI(+))m/e 431 (M+H)$^+$; $^1$H NMR (300 MHz, DMSO-D$_6$) δ ppm 6.92 (d, J=4.75 Hz, 1H) 7.35-7.46 (m, 1H) 7.51 (d, J=10.17 Hz, 1H) 7.57 (d, J=8.48 Hz, 2H) 7.67 (d, J=8.81 Hz, 2H) 8.38 (d, J=5.09 Hz, 1H) 8.64 (dd, J=7.29, 2.20 Hz, 1H) 8.98 (d, J=3.05 Hz, 1H) 9.41 (s, 1H).

EXAMPLE 18

N-[4-(3-amino-1H-pyrazolo[4,3-c]pyridin-4-yl)phenyl]-N'-[3-(trifluoromethyl)phenyl]urea

EXAMPLE 18A

N-[4-(2-chloro-3-cyanopyridin-4-yl)phenyl]-N'-[3-(trifluoromethyl)phenyl]urea and N-[4-(4-chloro-3-cyanopyridin-2-yl)phenyl]-N'-[3-(trifluoromethyl)phenyl]urea The tide compounds were prepared using the procedure described in Example 14D except using 1-isocyanato-3-trifluoromethyl-benzene instead of 1-fluoro-2-isocyanato-4-methyl-benzene.

EXAMPLE 18B

N-[4-(3-amino-1H-pyrazolo[4,3-c]pyridin-4-yl)phenyl]-N'-[3-(trifluoromethyl)phenyl]urea The title compound was prepared using the procedure described in Example 14E except using the mixture from Example 18A instead of the mixture from Example 14D. MS (ESI(+)) m/e 413 (M+H)$^+$; $^1$H NMR (300 MHz, DMSO-D$_6$) δ ppm 7.35 (d, J=7.46 Hz, 1H) 7.55 (t, J=7.80 Hz, 1H) 7.59-7.68 (m, 2H) 7.71-7.85 (m, J=8.93, 8.93, 8.93 Hz, 4H) 8.06 (s, 1H) 8.20 (s, 1H) 9.38 (s, 1H) 9.44 (s, 1H).

EXAMPLE 19

N-[4-(3-amino-1H-pyrazolo[3,4-b]pyridin-4-yl)phenyl]-N'-[3-(trifluoromethyl)phenyl]urea The title compound was prepared using the procedure described in Example 14E except using the mixture from Example 18A instead of the mixture from Example 14D. MS (ESI(+)) m/e 413 (M+H)$^+$; $^1$H NMR (300 MHz, DMSO-D$_6$) δ ppm 6.93 (d, J=4.75 Hz, 1H) 7.33 (d, J=7.46 Hz, 1H) 7.50-7.57 (m, 1H) 7.56 (d, J=8.47 Hz, 2H) 7.61 (d, J=8.48 Hz, 1H) 7.67 (d, J=8.81 Hz, 2H) 8.04 (s, 1H) 8.39 (d, J=4.75 Hz, 1H) 9.07 (s, 1H) 9.16 (s, 1H).

EXAMPLE 20

N-[4-(3-amino-1H-pyrazolo[4,3-c]pyridin-4-yl)phenyl]-N'-[4-fluoro-3-(trifluoromethyl)phenyl]urea

EXAMPLE 20A

N-[4-(2-chloro-3-cyanopyridin-4-yl)phenyl]-N'-[4-fluoro-3-(trifluoromethyl)phenyl]urea and compound with N-[4-(4-chloro-3-cyanopyridin-2-yl)phenyl]-N'-[4-fluoro-3-(trifluoromethyl)phenyl]urea The title compounds were prepared using the procedure described in Example 14D except using 1-fluoro-4-isocyanato-2-trifluoromethyl-benzene instead of 1-fluoro-2-isocyanato-4-methyl-benzene.

EXAMPLE 20B

N-[4-(3-amino-1H-pyrazolo[4,3-c]pyridin-4-yl)phenyl]-N'-[4-fluoro-3-(trifluoromethyl)phenyl]urea The title compound was prepared using the procedure described in Example 14E except using the mixture from Example 20A instead of the mixture from Example 14D. MS (ESI(+)) m/e 431 (M+H)$^+$; $^1$H NMR (300 MHz, DMSO-D$_6$) δ ppm 7.48 (t, J=9.83 Hz, 1H) 7.57-7.72 (m, J=16.28 Hz, 2H) 7.72-7.84 (m, 4H) 8.04 (dd, J=6.27, 2.54 Hz, 1H) 8.17-8.27 (m, 1H) 9.27 (s, 1H) 9.35 (s, 1H).

EXAMPLE 21

N-[4-(3-amino-1H-pyrazolo[3,4-b]pyridin-4-yl)phenyl]-N'-[4-fluoro-3-(trifluoromethyl)phenyl]urea The title compound was prepared using the procedure described in Example 14E except using the mixture from Example 20A instead of the mixture from Example 14D. MS (ESI(+)) m/e 431 (M+H)$^+$; $^1$H NMR (300 MHz, DMSO-D$_6$) δ ppm 6.93 (d, J=4.75 Hz, 1H) 7.46 (t, J=9.83 Hz, 1H) 7.56 (d, J=8.82 Hz, 2H) 7.67 (d, J=8.82 Hz, 2H) 7.67-7.71 (m, 1H) 8.03 (dd, J=6.44, 2.71 Hz, 1H) 8.40 (d, J=4.75 Hz, 1H) 9.11 (s, 1H) 9.17 (s, 1H).

EXAMPLE 22

N-[4-(3-amino-1H-pyrazolo[4,3-c]pyridin-4-yl)phenyl]-N'-(3,5-difluorophenyl)urea

EXAMPLE 22A

N-[4-(2-chloro-3-cyanopyridin-4-yl)phenyl]-N'-(3,5-difluorophenyl)urea and

N-[4-(4-chloro-3-cyanopyridin-2-yl)phenyl]-N'-(3,5-difluorophenyl)urea

The title compounds were prepared using the procedure described in Example 14D except using 3,5-difluoro-1-isocyanato-benzene instead of 1-fluoro-2-isocyanato-4-methyl-benzene.

EXAMPLE 22B

N-[4-(3-amino-1H-pyrazolo[4,3-c]pyridin-4-yl)phenyl]-N'-(3,5-difluorophenyl)urea The title compound was prepared using the procedure described in Example 14E except using the mixture from Example 22A instead of the mixture from Example 14D. MS (ESI(+)) m/e 381 (M+H)$^+$; $^1$H NMR (300 MHz, DMSO-D$_6$) δ ppm 6.84 (tt, J=9.41, 2.37, 2.20 Hz, 1H) 7.24 (dd, J=10.00, 2.20 Hz, 2H) 7.59-7.67 (m, 1H) 7.71-7.83 (m, 4H) 8.22 (s, 1H) 9.38 (s, 1 H) 9.44 (s, 1H).

EXAMPLE 23

N-[4-(3-amino-1H-pyrazolo[3,4-b]pyridin-4-yl)phenyl]-N'-(3,5-difluorophenyl)urea The title compound was prepared using the procedure described in Example 14E except using the mixture from Example 22A instead of the mixture from Example 14D. MS (ESI(+)) m/e 381 (M+H)$^+$; $^1$H NMR (300 MHz, DMSO-D$_6$) δ ppm 6.81 (tt, J=9.32, 2.37 Hz, 1H) 6.93 (d, J=4.75 Hz, 1H) 7.17-7.25 (m, 2H) 7.56 (d, J=8.82 Hz, 2H) 7.66 (d, J=8.82 Hz, 2H) 8.40 (d, J=4.75 Hz, 1H) 9.14 (s, 1H) 9.21 (s, 1H).

EXAMPLE 24

N-[4-(3-amino-1H-pyrazolo[4,3-c]pyridin-4-yl)phenyl]-N'-(3,5-dimethylphenyl)urea

EXAMPLE 24A

N-[4-(2-chloro-3-cyanopyridin-4-yl)phenyl]-N'-(3,5-dimethylphenyl)urea and

N-[4-(4-chloro-3-cyanopyridin-2-yl)phenyl]-N'-(3,5-dimethylphenyl)urea

The title compounds were prepared using the procedure described in Example 14D except using 3,5-dimethyl-1-isocyanato-benzene instead of 1-fluoro-2-isocyanato-4-methyl-benzene.

EXAMPLE 24B

N-[4-(3-amino-1H-pyrazolo[4,3-c]pyridin-4-yl)phenyl]-N'-(3,5-dimethylphenyl)urea The title compound was prepared using the procedure described in Example 14E except using the mixture from Example 24A instead of the mixture from Example 14D. MS (APCI(+)) m/e 373 (M+H)$^+$; $^1$H NMR (300 MHz, DMSO-D$_6$) δ ppm 2.25 (s, 6H) 6.66 (s, 1H) 7.11 (s, 2 H) 7.57-7.68 (m, 1H) 7.70-7.82 (m, 4H) 8.19-8.27 (m, 1H) 8.72 (s, 1H) 9.14 (s, 1H).

EXAMPLE 25

N-[4-(3-amino-1H-pyrazolo[3,4-b]pyridin-4-yl)phenyl]-N'-(3,5-dimethylphenyl)urea The title compound was prepared using the procedure described in Example 14E except using the mixture from Example 24A instead of the mixture from Example 14D. MS (ESI(+)) m/e 373 (M+H)$^+$; $^1$H NMR (300 MHz, DMSO-D$_6$) δ ppm 2.24 (s, 6H) 6.64 (s, 1H) 6.93 (d, J=4.75 Hz, 1H) 7.10 (s, 2H) 7.54 (d, J=8.48 Hz, 2H) 7.65 (d, J=8.48 Hz, 2H) 8.39 (d, J=5.09 Hz, 1H) 8.61 (s, 1H) 8.90 (s, 1H).

EXAMPLE 26

N-[4-(3-amino-1H-pyrazolo[4,3-c]pyridin-4-yl)phenyl]-N'-(3-methoxyphenyl)urea

EXAMPLE 26A

N-[4-(2-chloro-3-cyanopyridin-4-yl)phenyl]-N'-(3-methoxyphenyl)urea and

N-[4-(4-chloro-3-cyanopyridin-2-yl)phenyl]-N'-(3-methoxyphenyl)urea

The title compounds were prepared using the procedure described in Example 14D except using 1-isocyanato-3-methoxybenzene instead of 1-fluoro-2-isocyanato-4-methyl-benzene.

EXAMPLE 26B

N-[4-(3-amino-1H-pyrazolo[4,3-c]pyridin-4-yl)phenyl]-N'-(3-methoxyphenyl)urea

The title compound was prepared using the procedure described in Example 14E except using the mixture from Example 26A instead of the mixture from Example 14D. MS (ESI(+)) m/e 375 (M+H)$^+$; $^1$H NMR (300 MHz, DMSO-D$_6$) δ ppm 3.75 (s, 3H) 6.60 (dd, J=8.14, 2.37 Hz, 1H) 6.99 (d, J=7.46 Hz, 1H) 7.17-7.29 (m, 2H) 7.66 (d, J=6.78 Hz, 1H) 7.71-7.88 (m, 4 H) 8.20 (d, J=6.78 Hz, 1H) 8.99 (s, 1H) 9.28 (s, 1H).

EXAMPLE 27

N-[4-(3-amino-1H-pyrazolo[3,4-b]pyridin-4-yl)phenyl]-N'-(3-methoxyphenyl)urea

The title compound was prepared using the procedure described in Example 14E except using the mixture from Example 26A instead of the mixture from Example 14D. MS (ESI(+)) m/e 375 (M+H)$^+$; $^1$H NMR (300 MHz, DMSO-D$_6$) δ ppm 3.74 (s, 3H) 6.57 (dd, J=8.14, 1.70 Hz, 1H) 6.92 (d, J=4.75 Hz, 1H) 6.96 (dd, J=7.12, 2.03 Hz, 1H) 7.15-7.21 (m, 1H) 7.22 (d, J=2.37 Hz, 1H) 7.54 (d, J=8.82 Hz, 2H) 7.65 (d, J=8.81 Hz, 2H) 8.38 (d, J=4.75 Hz, 1H) 8.77 (s, 1H) 8.91 (s, 1H).

EXAMPLE 28

N-[4-(3-amino-1H-pyrazolo[4,3-c]pyridin-4-yl)phenyl]-N'-(3-chloro-4-fluorophenyl)urea

EXAMPLE 28A

N-[4-(2-chloro-3-cyanopyridin-4-yl)phenyl]-N'-(3-chloro-4-fluorophenyl)urea and

N-[4-(4-chloro-3-cyanopyridin-2-yl)phenyl]-N'-(3-chloro-4-fluorophenyl)urea

The title compounds were prepared using the procedure described in Example 14D except using 1-fluoro-2-chloro-4-isocyanato-benzene instead of 1-fluoro-2-isocyanato-4-methyl-benzene.

EXAMPLE 28B

N-[4-(3-amino-1H-pyrazolo[4,3-c]pyridin-4-yl)phenyl]-N'-(3-chloro-4-fluorophenyl)urea The title compound was prepared using the procedure described in Example 14E except using the mixture from Example 28A instead of the mixture from Example 14D. MS (ESI(+)) m/e 397 (M+H)$^+$; $^1$H NMR (300 MHz, DMSO-D$_6$) δ ppm 7.33-7.39 (m, 2H) 7.65 (d, J=6.44 Hz, 1H) 7.72-7.81 (m, 4H) 7.82-7.86 (m, 1H) 8.21 (s, 1H) 9.17 (s, 1H) 9.36 (s, 1H).

EXAMPLE 29

N-[4-(3-amino-1H-pyrazolo[3,4-b]pyridin-4-yl)phenyl]-N'-(3-chloro-4-fluorophenyl)urea The title compound was prepared using the procedure described in Example 14E except using the mixture from Example 28A instead of the mixture from Example 14D. MS (ESI(+)) m/e 397 (M+H)$^+$; $^1$H NMR (300 MHz, DMSO-D$_6$) δ ppm 6.93 (d, J=4.75 Hz, 1H) 7.32-7.38 (m, 2H) 7.55 (d, J=8.48 Hz, 2H) 7.66 (d, J=8.48 Hz, 2H) 7.81-7.85 (m, 1H) 8.39 (d, J=4.75 Hz, 1H) 8.99 (s, 1H) 9.04 (s, 1H).

EXAMPLE 30

N-[4-(3-amino-1H-pyrazolo[4,3-c]pyridin-4-yl)phenyl]-N'-(4-fluoro-3-methylphenyl)urea

EXAMPLE 30A

N-[4-(2-chloro-3-cyanopyridin-4-yl)phenyl]-N'-(4-fluoro-3-methylphenyl)urea and

N-[4-(4-chloro-3-cyanopyridin-2-yl)phenyl]-N'-(4-fluoro-3-methylphenyl)urea

The title compounds were prepared using the procedure described in Example 14D except using 1-fluoro-4-isocyanato-2-methyl-benzene instead of 1-fluoro-2-isocyanato-4-methyl-benzene.

EXAMPLE 30B

N-[4-(3-amino-1H-pyrazolo[4,3-c]pyridin-4-yl)phenyl]-N'-(4-fluoro-3-methylphenyl)urea The title compound was prepared using the procedure described in Example 14E except using the mixture from Example 30A instead of the mixture from Example 14D. MS (ESI(+)) m/e 377 (M+H)$^+$; $^1$H NMR (300 MHz, DMSO-D$_6$) δ ppm 2.23 (d, J=1.70 Hz, 3H) 7.08 (t, J=9.15 Hz, 1H) 7.24-7.34 (m, 1H) 7.39 (dd, J=6.95, 2.54 Hz, 1H) 7.65 (d, J=7.12 Hz, 1H) 7.68-7.83 (m, 4H) 8.19 (s, 1H) 8.89 (s, 1H) 9.25 (s, 1H).

EXAMPLE 31

N-[4-(3-amino-1H-pyrazolo[3,4-b]pyridin-4-yl)phenyl]-N'-(4-fluoro-3-methylphenyl)urea The title compound was prepared using the procedure described in Example 14E except using the mixture from Example 30A instead of the mixture from Example 14D. MS (ESI(+)) m/e 377 (M+H)$^+$; $^1$H NMR (300 MHz, DMSO-D$_6$) δ ppm 2.22 (d, J=1.70 Hz, 3H) 6.92 (d, J=4.75 Hz, 1H) 7.06 (t, J=9.15 Hz, 1H) 7.24-7.32 (m, 1H) 7.38 (dd, J=6.61, 2.54 Hz, 1H) 7.54 (d, J=8.82 Hz, 2H) 7.65 (d, J=8.82 Hz, 2H) 8.38 (d, J=4.75 Hz, 1H) 8.70 (s, 1H) 8.91 (s, 1H).

EXAMPLE 32

N-[4-(3-amino-1H-pyrazolo[4,3-c]pyridin-4-yl)phenyl]-N'-(3-methylphenyl)urea

EXAMPLE 32A

N-[4-(2-chloro-3-cyanopyridin-4-yl)phenyl]-N'-(3-methylphenyl)urea and

N-[4-(4-chloro-3-cyanopyridin-2-yl)phenyl]-N'-(3-methylphenyl)urea

The title compounds were prepared using the procedure described in Example 14D except using 1-methyl-3-isocyanato-benzene instead of 1-fluoro-2-isocyanato-4-methyl-benzene.

EXAMPLE 32B

N-[4-(3-amino-1H-pyrazolo[4,3-c]pyridin-4-yl)phenyl]-N'-(3-methylphenyl)urea

The title compound was prepared using the procedure described in Example 14E except using the mixture from Example 32A instead of the mixture from Example 14D. MS (ESI(+)) m/e 359 (M+H)$^+$; $^1$H NMR (300 MHz, DMSO-D$_6$) δ ppm 2.29 (s, 3H) 6.83 (d, J=7.12 Hz, 1H) 7.18 (t, J=7.63 Hz, 1H) 7.27 (d, J=8.14 Hz, 1H) 7.33 (s, 1H) 7.60 -7.84 (m, 5H) 8.20 (s, 1H) 8.85 (s, 1H) 9.22 (s, 1H).

EXAMPLE 33A-851301.2

N-[4-(3-amino-1H-pyrazolo[4,3-c]pyridin-4-yl)phenyl]-N'-(3-chlorophenyl)urea

EXAMPLE 33A

N-[4-(2-chloro-3-cyanopyridin-4-yl)phenyl]-N'-(3-chlorophenyl)urea and

N-[4-(4-chloro-3-cyanopyridin-2-yl)phenyl]-N'-(3-chlorophenyl)urea

The title compounds were prepared using the procedure described in Example 14D except using 1-chloro-3-isocyanato-benzene instead of 1-fluoro-2-isocyanato-4-methyl-benzene.

EXAMPLE 33B

N-[4-(3-amino-1H-pyrazolo[4,3-c]pyridin-4-yl)phenyl]-N'-(3-chlorophenyl)urea

The title compound was prepared using the procedure described in Example 14E except using the mixture from Example 33A instead of the mixture from Example 14D. MS (ESI(+)) m/e 359 (M+H)$^+$; $^1$H NMR (300 MHz, DMSO-D$_6$)

δ ppm 7.03-7.09 (m, 1H) 7.30-7.35 (m, 2 H) 7.64-7.82 (m, 7H) 8.21 (s, 1H) 9.24 (s, 1H) 9.42 (s, 1H).

EXAMPLE 34

N-[4-(3-amino-1H-pyrazolo[4,3-c]pyridin-4-yl)phenyl]-N'-(3-fluorophenyl)urea

EXAMPLE 34A

N-[4-(2-chloro-3-cyanopyridin-4-yl)phenyl]-N'-(3-fluorophenyl)urea and

N-[4-(4-chloro-3-cyanopyridin-2-yl)phenyl]-N'-(3-fluorophenyl)urea

The title compounds were prepared using the procedure described in Example 14D except using 1-fluoro-3-isocyanato-benzene instead of 1-fluoro-2-isocyanato-4-methylbenzene.

EXAMPLE 34B

N-[4-(3-amino-1H-pyrazolo[4,3-c]pyridin-4-yl)phenyl]-N'-(3-fluorophenyl)urea

The title compound was prepared using the procedure described in Example 14E except using the mixture from Example 34A instead of the mixture from Example 14D. MS (ESI(+)) m/e 363 (M+H)+; $^1$H NMR (300 MHz, DMSO-D$_6$) δ ppm 6.82 (td, J=8.31, 2.03 Hz, 1H) 7.17 (d, J=8.14 Hz, 1H) 7.26-7.43 (m, 1H) 7.47-7.57 (m, J=12.04, 2.20, 2.03 Hz, 1H) 7.59-7.67 (m, 1H) 7.70-7.83 (m, 4H) 8.22 (s, 1H) 9.17 (s, 1H) 9.31 (s, 1H).

EXAMPLE 35

N-[4-(3-amino-1H-pyrazolo[3,4-b]pyridin-4-yl)phenyl]-N'-(3-methylphenyl)urea

EXAMPLE 35A

2-[1-(4-nitrophenyl)ethylidene]malononitrile

A mixture of 1-(4-Nitro-phenyl)ethanone (10 g, 60.5 mmol), malononitrile (4 g, 60.5 mmol), NH$_4$OAc (4.66 g, 121 mmol) in benzene (100 mL) and acetic acid (6.4 mL) was refluxed overnight using a Dean Stark to collect water. The reaction was allowed to cool to r.t., partitioned between water and EtOAc (3×). the combined organic were washed with brine, dried (Na$_2$SO$_4$), concentrated and purified via silica gel chromatography eluting with 3 to 1 hexanes:EtOAc to give 3.71 g (29%) of the title compound. R$_f$=0.22 (4:1 hexanes: EtOAc).

EXAMPLE 35B

2-Chloro-4-(4-nitro-phenyl)-nicotinonitrile

A solution of Example 35A 95.83 g, 27.4 mmol) in CH$_2$Cl$_2$ (100 mL) was treated with dimethoxymethyl-dimethylamine (7.3 mL, 54.7 mmol), stirred overnight at r.t. then concentrated. The residue was dissolved in acetic acid (200 mL) then treated with HCl gas (bubbled through for ca. 4 minutes). The resulting mixture was stirred at room temperature for 4 h resulting in a thick suspension which poured onto ice water. The precipitate formed was collected via filtration, then suspended in sat. aq. NaHCO$_3$ and extracted with EtOAc (3×130 mL). Most of the solid remained undissolved and was collected by filtration then washed sequentially with water and EtOAc to give 4.00 g of example 35B. The organic extracts were washed with brine, dried (MgSO$_4$), concentrated and purified via silica gel chromatography eluting with 40% EtOAc-hexanes to give an additional 0.42 g of the title compound. MS (ESI(+)) m/e 260 (M+H)+.

EXAMPLE 35C 4-(4-Amino-phenyl)-2-chloro-nicotinonitrile

A mixture of Example 35B (2.0 g), iron powder (2.15 g) and NH$_4$Cl (0.4 g) in EtOH (80 mL), water (20 mL) and THF (80 mL) was refluxed overnight, then filtered through a pad of celite while still hot The filter cake was washed with EtOH and the combined filtrates were concentrated. The residue was triturated from water to give 1.46 g of example 35C. R$_f$=0.41 (1:1 hexanes: EtOAc).

EXAMPLE 35D

1-[4-(2-Chloro-3-cyano-pyridin-4-yl)-phenyl]-3-m-tolyl-urea

A mixture of Example 35C (0.1 g, 0.43 mmol), 1-isocyanato-3-methylbenzene (0.06 mL, 0.43 mmol) in CH$_2$Cl$_2$ (3 mL) and THF (3 mL) was stirred at room temperature overnight, then treated with an additional 0.02 mL of 1-isocyanato-3-methylbenzene, stirred for 5 more hours at room temperature then for 2.5 h at 50° C. The resulting precipitate was collected via filtration to give 0.1 g of the title compound. MS (ESI(+)) m/e 363 (M+H)+.

EXAMPLE 35E

N-[4-(3-amino-1H-pyrazolo[3,4-b]pyridin-4-yl)phenyl]-N'-(3-methylphenyl)urea

A mixture of Example 35D (0.08 g, 0.22 mmol) and hydrazine hydrate (0.11 mL, 2.2 mmol) in n-butanol (5 mL) was heated at 110° C. for 2 h, then concentrated. The residue was purified via HPLC on an Agilent Zorbax Stablebond C-18 (7 micron particle size) preparative column using a solvent gradient of 20% to 100% acetonitrile in 0.1% aqueous TFA at a flow rate of 15 ml/min over 50 min, to give the title compound. $^1$H NMR (500 MHz, DMSO-D$_6$) δ ppm 2.29 (s, 3H) 6.81 (d, J=7.32 Hz, 1H) 6.93 (d, J=4.58 Hz, 1H) 7.17 (t, J=7.63 Hz, 1H) 7.26 (d, J=7.63 Hz, 1H) 7.33 (s, 1H) 7.54 (d, J=8.24 Hz, 2H) 7.66 (d, J=7.93 Hz, 2H) 8.38 (d, J=4.27 Hz, 1H) 8.80 (s, 1H) 9.04 (s, 1H); MS (ESI(+)) m/e 359 (M+H)+.

EXAMPLE 36

N-[4-(3-amino-1H-pyrazolo[3,4-b]pyridin-4-yl)phenyl]-N'-(4-methylphenyl)urea

The title compound was prepared using the procedures described in Examples 35D and 35E using 1-isocyanato-4-methylbenzene instead of 1-isocyanato-3-methylbenzene in Example 35D. $^1$H NMR (300 MHz, DMSO-D$_6$) δ ppm 2.25 (s, 3H) 6.93 (d, J=4.75 Hz, 1H) 7.10 (d, J=8.14 Hz, 2H) 7.36 (d, J=8.48 Hz, 2H) 7.54 (d, J=8.82 Hz, 2. H) 7.65 (d, J=8.82 Hz, 2H) 8.40 (d, J=5.09 Hz, 1H) 8.70 (s, 1H) 8.94 (s, 1H). MS (ESI(+)) m/e 359 (M+H)+.

EXAMPLE 37

N-[4-(3-amino-1H-pyrazolo[3,4-b]pyridin-4-yl)phenyl]-N'-(2-methylphenyl)urea

The title compound was prepared using the procedures described in Examples 35D and 35E using 1-isocyanato-2-methylbenzene instead of 1-isocyanato-3-methylbenzene in Example 35. $^1$H NMR (300 MHz, DMSO-D$_6$) δ ppm 2.27 (s, 3H) 6.89-7.03 (m, 2H) 7.11-7.24 (m, 2 H) 7.56 (d, J=8.82 Hz, 2H) 7.67 (d, J=8.82 Hz, 2H) 7.83 (d, J=7.12 Hz, 1H) 8.04 (s, 1H) 8.41 (d, J=5.09 Hz, 1H) 9.29 (s, 1H). MS (ESI(+)) m/e 359 (M+H)$^+$.

EXAMPLE 38

N-[4-(3-amino-1H-pyrazolo[3,4-b]pyridin-4-yl)phenyl]-N'-thien-3-ylurea

The title compound was prepared using the procedures described in Examples 35D and 35E using 3-isocyanatothiophene instead of 1-isocyanato-3-methylbenzene in Example 35D. $^1$H NMR (300 MHz, DMSO-D$_6$) δ ppm 6.95 (d, J=4.75 Hz, 1H) 7.08 (dd, J=5.43, 1.36 Hz, 1H) 7.32 (dd, J=3.39, 1.36 Hz, 1H) 7.45 (dd, J=5.26, 3.22 Hz, 1H) 7.55 (d, J=8.82 Hz, 1H) 7.67 (d, J=8.82 Hz, 1H) 8.41 (d, J=4.75 Hz, 1H) 8.96 (s, 1H) 9.09 (s, 1H). MS (ESI(+) m/e 351 (M+H)$^+$.

EXAMPLE 39

N-[4-(3-amino-1H-pyrazolo[3,4-b]pyridin-4-yl)phenyl]-N'-(3-chlorophenyl)urea

The title compound was prepared using the procedures described in Examples 35D and 35E using 1-chloro-3-isocyanatobenzene instead of 1-isocyanato-3-methylbenzene in Example 35D. $^1$H NMR (300 MHz, DMSO-D$_6$) δ ppm 6.92 (d, J=4.75 Hz, 1H) 7.00-7.07 (m, 1H) 7.28-7.34 (m, 2H) 7.55 (d, J=8.48 Hz, 2H) 7.65 (d, J=6.78 Hz, 2H) 7.74 (s, 1H) 8.38 (d, J=4.75 Hz, 1H) 9.00 (s, 1H) 9.03 (s, 1H). MS (ESI(+)) m/e 379 (M+H)$^+$.

EXAMPLE 40

4-(4-aminophenyl)-1-methyl-1H-pyrazolo[3,4-b]pyridin-3-amine

The title compound was prepared using the procedure described in Example 6A using the product of Example 35C instead the product of Example 1C. MS (ESI(+)) m/e 240 (M+H)$^+$.

EXAMPLE 41

N-[4-(3-amino-1-methyl-1H-pyrazolo[3,4-b]pyridin-4-yl)phenyl]-N'-(3-methylphenyl)urea A solution of Example 40 (87 mg, 0.36 mml) and 1-isocyanato-3-methylbenzene (0.046 mL, 0.36 mmol) in THF (3 mL), CH$_2$Cl$_2$ (3 mL) was stirred at room temperature for 5 h. The resulting precipitate was filtered off and purified via HPLC on an Agilent Zorbax Stablebond C-18 (7 micron particle size) preparative column using a solvent gradient of 20% to 100% acetonitrile in 0.1% aqueous TFA at a flow rate of 15 ml/min over 50 min, to give the 62 mg of the title compound. $^1$H NMR (300 MHz, DMSO-D$_6$) δ ppm 2.29 (s, 3H) 3.83 (s, 3H) 6.81 (d, J=7.46 Hz, 1H) 6.92 (d, J=4.75 Hz, 1H) 7.17 (t, J=7.80 Hz, 1H) 7.26 (d, J=8.48 Hz, 1H) 7.32 (s, 1H) 7.53 (d, J=8.81 Hz, 2H) 7.65 (d, J=8.82 Hz, 2H) 8.40 (d, J=4.75 Hz, 1H) 8.67 (s, 1H) 8.90 (s, 1H). MS (ESI(+)) m/e 373 (M+H)$^+$.

EXAMPLE 42

N-[4-(3-amino-1-methyl-1H-pyrazolo[3,4-b]pyridin-4-yl)phenyl]-N'-(3-fluorophenyl)urea The title compound was prepared using the procedure described in Example 41 using 1-fluoro-3-isocyanatobenzene instead of 1-isocyanato-3-methylbenzene. $^1$H NMR (300 MHz, DMSO-D6) δ ppm 3.83 (s, 3H) 6.80 (td, J=8.56, 2.20 Hz, 1H) 6.92 (d, J=4.75 Hz, 1H) 7.15 (d, J=9.49 Hz, 1H) 7.25-7.39 (m, 1H) 7.46-7.58 (m, 3H) 7.65 (d, J=8.82 Hz, 2H) 8.40 (d, J=4.75 Hz, 1H) 9.00 (s, 2H). MS (ESI(+)) m/e 377 (M+H)$^+$.

EXAMPLE 43

N-[4-(3-amino-1-methyl-1H-pyrazolo[3,4-b]pyridin-4-yl)phenyl]-N'-[3-trifluoromethyl)phenol]urea The title compound was prepared using the procedure described in Example 41 using 1-isocyanato-3-trifluoromethylbenzene instead of 1-isocyanato-3-methylbenzene. $^1$H NMR (300 MHz, DMSO-D$_6$) δ ppm 3.84 (s, 3H) 6.94 (d, J=4.75 Hz, 1H) 7.33 (d, J=7.46 Hz, 1H) 7.47-7.65 (m, 4H) 7.68 (d, J=6.78 Hz, 2H) 8.04 (s, 1H) 8.42 (d, J=4.75 Hz, 1H) 9.10 (s, 1H) 9.18 (s, 1H). MS (ESI(+)) m/e 427 (M+H)$^+$.

EXAMPLE 44

N-[4-(3-amino-1-methyl-1H-pyrazolo[3,4-b]pyridin-4-yl)phenyl]-N'-[2-fluoro-5-(trifluoromethyl)phenyl]urea The title compound was prepared using the procedure described in Example 41 using 1-fluoro-2-isocyanato-4-trifluoromethylbenzene instead of 1-isocyanato-3-methylbenzene. $^1$H NMR (300 MHz, DMSO-D$_6$) δ ppm 3.83 (s, 3H) 4.70 (s, 2H) 6.93 (d, J=4.75 Hz, 1H) 7.36-7.46 (m, 1H) 7.47-7.61 (m, 3H) 7.67 (d, J=8.48 Hz, 2H) 8.41 (d, J=4.75 H, 1H) 8.64 (dd, J=7.46, 2.37 Hz, 1H) 8.99 (s, 1H) 9.42 (s, 1H). MS (ESI(+)) m/e 445 (M+H)$^+$.

EXAMPLE 45

N-[4-(3-amino-1-methyl-1H-pyrazolo[3,4-b]pyridin-4-yl)phenyl]-N'-(4-fluoro-3-methylphenyl)urea The title compound was prepared using the procedure described in Example 41 using 1-fluoro-2-methyl-4-isocyanatobenzene instead of 1-isocyanato-3-methylbenzene. $^1$H NMR (300 MHz, DMSO-D$_6$) δ ppm 2.22 (d, J=2.03 Hz, 3H) 3.83 (s, 3H) 6.92 (d, J=4.75 Hz, 1H) 7.06 (t, J=9.15 Hz, 1H) 7.24-7.32 (m, 1H) 7.38 (dd, J=6.78, 2.37 Hz, 1H) 7.53 (d, J=8.48 Hz, 2H) 7.65 (d, J=8.81 Hz, 2H) 8.40 (d, J=4.75 Hz, 1H) 8.74 (s, 1H) 8.95 (s, 1H). MS (ESI(+)) m/e 391 (M+H)$^+$.

EXAMPLE 46

N-[4-(3-amino-1-methyl-1H-pyrazolo[3,4-b]pyridin-4-yl)phenyl]-N'-(3-bromophenyl) urea The title compound was prepared using the procedure described in Example 41 using 1-bromo-3-isocyanatobenzene instead of 1-isocyanato-3-methylbenzene. $^1$H NMR (300 MHz, DMSO-D$_6$) δ ppm 3.83 (s, 3H) 6.92 (d, J=4.75 Hz, 1H) 7.17 (d, J=7.80 Hz, 1H) 7.26 (t, J=7.97 Hz, 1H) 7.34 (d, J=8.14 Hz, 1H) 7.54 (d, J=8.48 Hz, 2H) 7.65 (d, J=8.82 Hz, 2H) 7.84-7.90 (m, 1H) 8.40 (d, J=4.75 Hz, 1H) 8.97 (s, 1H) 9.01 (s, 1H). MS (ESI(+)) m/e 439 (M+H)$^+$.

EXAMPLE 47

N-[4-(3-amino-1-methyl-1H-pyrazolo[3,4-b]pyridin-4-yl)phenyl]-N'-(3,5-dimethylphenyl)urea The title compound was prepared using the procedure described in Example 41 using 1-isocyanato-3,5-dimethylbenzene instead of 1-isocyanato-3-methylbenzene. $^1$H NMR (300 MHz, DMSO-$D_6$) δ ppm 2.24 (s, 6H) 3.84 (s, 3H) 6.63 (s, 1H) 6.93 (d, J=4.75 Hz, 2H) 7.10 (s, 2H) 7.53 (d, J=8.48 Hz, 2H) 7.65 (d, J=8.81 Hz, 5H) 8.41 (d, J=4.75 Hz, 1H) 8.66 (s, 1H) 8.96 (s, 1H). MS (ESI(+)) m/e 387 (M+H)$^+$.

EXAMPLE 48

N-[4-(3-amino-1-methyl-1H-pyrazolo[3,4-b]pyridin-4-yl)phenyl]-N'-(3,4-dichlorophenyl)urea The title compound was prepared using the procedure described in Example 41 using 1,2-dichloro-4-isocyanatobenzene instead of 1-isocyanato-3-methylbenzene. $^1$H NMR (300 MHz, DMSO-$D_6$) δ ppm 3.83 (s, 3H) 6.92 (d, J=4.75 Hz, 1H) 7.36 (dd, J=8.81, 2.37 Hz, 1H) 7.50-7.58 (m, 3H) 7.65 (d, J=8.81 Hz, 2H) 7.90 (d, J=2.37 Hz, 1H) 8.40 (d, J=4.75 Hz, 1H) 9.07 (s, 1H) 9.09 (s, 3H). MS (ESI(+)) m/e 427 (M+H)$^+$.

EXAMPLE 49

N-[4-(3-amino-1-methyl-1H-pyrazolo[3,4-b]pyridin-4-yl)phenyl]-N'-[4-fluoro-3-(trifluoromethyl)phenyl]urea The title compound was prepared using the procedure described in Example 41 using 1-fluoro-4-isocyanato-2-trifluoromethylbenzene instead of 1-isocyanato-3-methylbenzene. $^1$H NMR (300 MHz, DMSO-$D_6$) δ ppm 3.83 (s, 3H) 6.93 (d, J=4.75 Hz, 1H) 7.45 (t, J=9.83 Hz, 1 H) 7.55 (d, J=8.48 Hz, 2H) 7.63-7.70 (m, 3H) 8.03 (dd, J=6.78, 2.71 Hz, 1H) 8.41 (d, J=4.75 Hz, 1H) 9.08 (s, 1H) 9.14 (s, 1H). MS (ESI(+)) m/e 445 (M+H)$^+$.

What is claimed is:

1. A compound of formula (II)

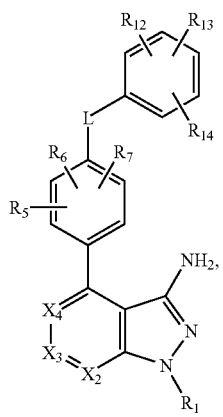

(II)

or a therapeutically acceptable salt thereof, wherein
$X_2$ is selected from the group consisting of N and $CR_2$;
$X_3$ is selected from the group consisting of N and $CR_3$;
$X_4$ is selected from the group consisting of N and $CR_4$;
provided that only one of $X_2$, $X_3$, and $X_4$ is N;
$R_1$ is selected from the group consisting of hydrogen, alkoxyalkyl, alkoxycarbonyl, alkenyl, alkyl, alkylcarbonyl, aryl, arylalkyl, heteroaryl, heteroarylalkyl, heterocyclealkyl, hydroxyalkyl, $(NR_AR_B)$carbonyl, $(NR_AR_B)$sulfonyl, and $(NR_AR_B)$sulfonylalkyl;
$R_2$ is selected from the group consisting of hydrogen, alkoxy, alkoxyalkoxy, alkoxyalkyl, alkyl, aryl, arylalkyl, aryloxy, aryloxyalkyl, halo, haloalkoxy, haloalkyl, heteroaryl, heteroarylalkenyl, heteroarylalkoxy, heteroarylealkyl, heteroaryloxyalkyl, heterocycle, heterocyclealkenyl, heterocyclealkoxy, heterocyclealkyl, heterocycleoxyalkyl, hydroxy, hydroxyalkoxy, hydroxyalkyl, $(NR_CR_D)$alkenyl, $(NR_CR_D)$alkoxy, $(NR_CR_D)$alkyl, $(NR_CR_D)$alkynyl, $(NR_CR_D)$carbonylalkenyl, and $(NR_CR_D)$carbonylalkyl;
$R_3$ and $R_4$ are independently selected from the group consisting of hydrogen, alkoxy, alkoxyalkoxy, alkoxyalkyl, alkyl, arylalkyl, aryloxy, aryloxyalkyl, halo, haloalkoxy, haloalkyl, heteroarylalkenyl, heteroarylalkoxy, heteroarylealkyl, heteroaryloxyalkyl, heterocycle, heterocyclealkenyl, heterocyclealkoxy, heterocyclealkyl, heterocycleoxyalkyl, hydroxy, hydroxyalkoxy, hydroxyalkyl, $(NR_CR_D)$alkenyl, $(NR_CR_D)$alkoxy, $(NR_CR_D)$alkyl, $(NR_CR_D)$alkynyl, $(NR_CR_D)$carbonylalkenyl, and $(NR_CR_D)$carbonylalkyl;
$R_5$, $R_6$, and $R_7$ are independently selected from the group consisting of hydrogen, alkoxy, alkoxyalkoxy, alkyl, halo, haloalkoxy, haloalkyl, hydroxy, and —$NR_ER_F$;
L is selected from the group consisting of $(CH_2)_mN(R_{10})$ $C(O)N(R_{11})(CH_2)_n$, and $CH_2C(O)NR_{10}$, wherein each group is drawn with its left end attached to the phenyl ring substituted with $R_5$, $R_6$, and $R_7$;
m and n are independently 0 or 1;
$R_{10}$ and $R_{11}$ are independently selected from the group consisting of hydrogen and alkyl;
$R_{12}$, $R_{13}$, and $R_{14}$ are independently selected from the group consisting of hydrogen, alkenyl, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylthio, alkylthioalkyl, alkynyl, carboxy, carboxyalkyl, cyano, cyanoalkyl, ethylenedioxy, formyl, haloalkoxy, haloalkyl, halogen, hydroxy, hydroxyalkyl, mercapto, methylenedioxy, nitro, —$NR_GR_H$, $(NR_GR_H)$carbonyl, and $(NR_GR_H)$sulfonyl;
$R_A$ and $R_B$ are independently selected from the group consisting of hydrogen and alkyl;
$R_C$ and $R_D$ are independently selected from the group consisting of hydrogen, alkenyl, alkyl, alkylcarbonyl, alkylsulfonyl, aryl, arylalkyl, arylcarbonyl, arylsulfonyl, haloalkylsulfonyl, cycloalkyl, cycloalkylalkyl, heteroaryl, heteroarylalkyl, heteroarylsulfonyl, heterocycle, heterocyclealkyl, and heterocyclesulfonyl;
$R_E$ and $R_F$ are independently selected from the group consisting of hydrogen, alkyl, and alkylcarbonyl; and
$R_G$ and $R_H$ are independently selected from the group consisting of hydrogen, alkyl, alkylcarbonyl, aryl, and arylalkyl.

2. The compound according to claim 1 wherein
$X_2$ is N;
$X_3$ is $CR_3$; and
$X_4$ is $CR_4$.

3. The compound according to claim 1 wherein
$X_2$ is $CR_2$;
$X_3$ is N; and
$X_4$ is $CR_4$.

4. The compound according to claim 1 wherein
$X_2$ is $CR_2$;
$X_3$ is $CR_3$; and
$X_4$ is N.

* * * * *

UNITED STATES PATENT AND TRADEMARK OFFICE
CERTIFICATE OF CORRECTION

PATENT NO. : 7,812,166 B2
APPLICATION NO. : 11/261814
DATED : October 12, 2010
INVENTOR(S) : Dai et al.

It is certified that error appears in the above-identified patent and that said Letters Patent is hereby corrected as shown below:

Column 44, line 7, claim 1: "heteroarylealkyl" to read as --heteroarylalkyl--

Column 44, line 17, claim 1: "heteroarylealkyl" to read as --heteroarylalkyl--

Signed and Sealed this
Third Day of May, 2011

David J. Kappos
*Director of the United States Patent and Trademark Office*